US010106836B2

(12) United States Patent
Lo et al.

(10) Patent No.: US 10,106,836 B2
(45) Date of Patent: Oct. 23, 2018

(54) DETERMINING FETAL GENOMES FOR MULTIPLE FETUS PREGNANCIES

(71) Applicant: The Chinese University of Hong Kong, Sha Tin, New Territories (CN)

(72) Inventors: Yuk Ming Dennis Lo, Kowloon (CN); Wai Kwun Rossa Chiu, Shatin (CN); Kwan Chee Chan, Kowloon (CN)

(73) Assignee: The Chinese University of Hong Kong, Shatin, New Territories (HK)

( * ) Notice: Subject to any disclaimer, the term of this patent is extended or adjusted under 35 U.S.C. 154(b) by 670 days.

(21) Appl. No.: 14/216,405

(22) Filed: Mar. 17, 2014

(65) Prior Publication Data

US 2014/0315200 A1 Oct. 23, 2014

Related U.S. Application Data

(60) Provisional application No. 61/789,992, filed on Mar. 15, 2013.

(51) Int. Cl.
*C12Q 1/68* (2018.01)
*G06F 19/22* (2011.01)
*C12Q 1/6883* (2018.01)

(52) U.S. Cl.
CPC .............. *C12Q 1/68* (2013.01); *C12Q 1/6883* (2013.01); *C12Q 2600/156* (2013.01); *G06F 19/22* (2013.01)

(58) Field of Classification Search
None
See application file for complete search history.

(56) References Cited

U.S. PATENT DOCUMENTS

| | | | |
|---|---|---|---|
| 6,258,540 B1 | 7/2001 | Lo et al. |
| 6,927,028 B2 | 8/2005 | Dennis et al. |
| 7,727,720 B2 | 6/2010 | Dhallan |
| 8,467,976 B2 | 6/2013 | Lo et al. |
| 2005/0164241 A1 | 7/2005 | Hahn |
| 2006/0252071 A1 | 11/2006 | Lo et al. |
| 2007/0202525 A1 | 8/2007 | Quake et al. |
| 2008/0070792 A1 | 3/2008 | Stoughton et al. |
| 2008/0318235 A1 | 12/2008 | Handyside |
| 2009/0029377 A1 | 1/2009 | Lo et al. |
| 2009/0087847 A1 | 4/2009 | Lo et al. |
| 2010/0112590 A1 | 5/2010 | Lo |
| 2011/0086769 A1 | 4/2011 | Oliphant et al. |
| 2011/0105353 A1 | 5/2011 | Lo et al. |
| 2011/0178719 A1 | 7/2011 | Rabinowitz et al. |
| 2011/0276277 A1 | 11/2011 | Lo |
| 2011/0288780 A1 | 11/2011 | Rabinowitz et al. |
| 2013/0029852 A1 | 1/2013 | Rava et al. |
| 2013/0059733 A1 | 3/2013 | Lo et al. |

FOREIGN PATENT DOCUMENTS

| | | |
|---|---|---|
| CN | 102770558 A | 11/2012 |
| TW | 201243326 A | 11/2012 |

| | | |
|---|---|---|
| WO | 2004/078999 | 9/2004 |
| WO | 2007/028155 | 3/2007 |
| WO | 2007/100911 | 9/2007 |
| WO | 2009/013492 | 1/2009 |
| WO | 2010/075459 A1 | 7/2010 |
| WO | 2011/057094 A1 | 5/2011 |
| WO | 2012/103031 A2 | 8/2012 |
| WO | 2014139477 A1 | 9/2014 |

OTHER PUBLICATIONS

Canick et al. DNA sequencing of maternal plasma to identify Down syndrome and other trisomies in multiple gestations Prenatal Diagnosis vol. 32, pp. 730-734 (2012).*
Sehnert et al. Optimal Detection of Fetal Chromosomal Abnormalities by Massively Parallel DNA Sequencing fo Cell-Free DNA from Maternal Blood Clinical Chemistry vol. 57, pp. 1042-1049 (2011).*
Lau et al. Non-invasive prenatal screening of fetal Down syndrome by maternal plasma DNA sequencing in twin pregnancies the Journal of Maternal-Fetal and Neonatal Medicine vol. 26, pp. 434-437 (2013).*
Kitzman et al. Noninvasive Whole-Genome Sequencing of a Human Fetus Science Translational Medicine vol. 4, article 137ra76 (2012).*
International Search Report and Written Opinion dated Jun. 27, 2014 in PCT/CN2014/073506, 15 pages.
Amicucci, P., et al., "Prenatal Diagnosis of Myotonic Dystrophy Using Fetal DNA Obtained from Maternal Plasma," Clin Chem, 2000, vol. 46, No. 2, pp. 301-302.
Attilakos, George, et al., "Quantification of free fetal DNA in multiple pregnancies and relationship with chorionicity," Prenatal Diagnosis, 2011, pp. 967-972, vol. 31.
Batzer, M. A., et al., "Enhanced evolutionary PCR using oligonucleotides with inosine at the 3'-terminus," Nucleic Acid Res., Jul. 12, 1991, vol. 19, p. 5081.
Bentley, D.R., et al., "Accurate whole human genome sequencing using reversible terminator chemistry," Nature, Nov. 2008; vol. 456, pp. 53-59.

(Continued)

*Primary Examiner* — John S Brusca
(74) *Attorney, Agent, or Firm* — Kilpatrick Townsend & Stockton LLP

(57) ABSTRACT

Techniques are provided for determining inheritance of maternal and paternal haplotypes in preganncies with multiple fetuses. Maternal inheritance can be determined at loci where the mother is heterozygous and the paternally inherited alleles are known (e.g., the father is homozygous). Two types of loci may be used, where one type has the paternal allele appear on a first maternal haplotype, and another type has the paternal allele appear on a second maternal haplotype. Paternal inheritance can be determined from loci where the father is heterozygous and the maother is homozygous. Amounts of different alleles at each locus can be measured. A comparison of the amounts (e.g., using a fractional concentration of each allele and cutoffs) can be used to determine the haplotype inheritance. A haplotype can be linked to a condition of interest.

58 Claims, 17 Drawing Sheets

(56) References Cited

OTHER PUBLICATIONS

Bianchi, Diana W., et al., "Large amounts of cell-free fetal DNA are present in amniotic fluid," Clinical Chemistry, 2001, vol. 47, No. 10, pp. 1867-1869.
Botezatu, I., et al., "Genetic Analysis of DNA Excreted in Urine: a New Approach for Detecting Specific Genomic DNA Sequences from Cells Dying in an Organism," Clin Chem, 2000; vol. 46, pp. 1078-1084.
Braun, Siegmund Lorenz, et al., "Plasma Troponin and Troponin I after Minimally Invasive Coronary Bypass Surgery," Clinical Chemistry, 2000, vol. 46, No. 2, pp. 279-302.
Chan, F.Y., et al., "Prenatal RHD gene determination and dosage analysis by PCR: clinical evaluation," Prenatal Diagnosis, 2001, vol. 21, pp. 321-326.
Chan, K.C.A., et al., "Size Distributions of Maternal and Fetal DNA in Maternal Plasma," Clin Chem, 2004; vol. 50, pp. 88-92.
Chan, K.C.A., et al.; "Hypermethylated Rassfia in Maternal Plasma: A Universal Fetal DNA Marker that Improves the Reliability of Noninvasive Prenatal Diagnosis"; Clin Chem, 2006, vol. 52, pp. 2211-2218.
Chauhan, Suneet, P., et al., "Twins: Prevalence, problems, and preterm births," Am J Obstet Gynecol, Oct. 2010; vol. 203, pp. 305-315.
Chen, Chih-Ping, et al., "Rapid determination of zygosity and common aneuploidies from amniotic fluid cells using quantitative fluorescent polymerase chain reaction following genetic amniocentesis in multiple pregnancies," Human Reproduction, 2000;vol. 15, No. 4, pp. 929-934.
Chim, Stephen S.C., et al., "Detection of the placental epigenetic signature of the maspin gene in maternal plasma," PNAS USA, Oct. 2011, vol. 102, pp. 14753-14758.
Chiu, Rossa W.K., et al., "Non-invasive prenatal diagnosis by single molecule counting technologies," Trends Genet, 2009; vol. 25, pp. 324-331.
Chiu, Rossa W.K., et al., "Noninvasive prenatal diagnosis of fetal chromosomal aneuploidy by massively parallel genomic sequencing of DNA in maternal plasma," PNAS USA, 2008, vol. 105, pp. 20458-20463.
Chiu, Rossa W.K., et al., "Prenatal exclusion of β thalassaemia major by examination of maternal plasma," The Lancet, 2002; vol. 360, pp. 998-1000.
Chiu, Rossa W.K., et al., "Hypermethylation of RASSF1A in Human and Rhesus Placentas," The American Journal of Pathology, Mar. 2007, vol. 170, No. 3, pp. 941-950.
Clark, Andres, "Inference of haplotypes from PCR-amplified samples of dipllid populations," Mol Biol Evol, 1990, vol. 7, pp. 111-122.
Clarke, J., et al., "Continuous base identification for single-molecule nanopore DNA sequencing," Nat Nanotechnol, [online], Apr. 2009; vol. 4, pp. 265-270.
Ding, C., et al., "Direct molecular haplotyping of long-range genomic DNA with M1-PCR," Proc Natl Acad Sci USA, Jun. 24, 2003; vol. 100, pp. 7449-7453.
Ding, Chunming, et al., "MS Analysis of Single-Nucleotide Differences in Circulating Nucleic Acids: Application to Noninvasive Prenatal Diagnosis," Jul. 20, 2004, Proceedings of the National Academy of Sciences of the United States of America, vol. 101, No. 29, pp. 10762-10767.
Eid, J., et al., "Real-Time DNA Sequencing from Single Polymerase Molecules," Science, Jan. 2, 2009, vol. 323, pp. 133-138.
Fan, H. Christina, et al., "Noninvasive diagnosis of fetal aneuploidy by shotgun sequencing DNA from maternal blood," PNAS USA, 2008, vol. 105, pp. 16266-16271.
Finning, K.M, et al., "Prediction of fetal D status from maternal plasma: introduction of a new noninvasive fetal RHD genotyping service," Transfusion, Aug. 2002, pp. 1079-1085, vol. 42.
Geiss, G.K., et al., "Direct multiplexed measurement of gene expression with color-coded probe pairs," Nat Biotechnol, Mar. 2008, vol. 26, pp. 317-325.

Ghanta, Sujana, et al., "Non-Invasive Prenatal Detection of Trisomy 21 Using Tandem Single Nucleotide Polymorphisms," PloS One, Oct. 2010, 10 pages, vol. 5, Issue 10.
Gnirke, A., et al., "Solution hybrid selection with ultra-long oligonucleotides for massively parallel targeted sequencing," Nat Biotechnol, Feb. 2009, vol. 27, No. 2, pp. 182-189.
Guilherme, R., et al., "Zygosity and chorionicity in triplet pregnancies: new data," Human Reproduction, 2009, vol. 24, pp. 100-105.
Harris, T. D., et al.; "Single-Molecule DNA Sequencing of a Viral Genome"; Science, Apr. 4, 2008, vol. 320, pp. 106-109.
Illanes, S., et al., "Detection of cell-free fetal DNA in maternal urine," Prenatal Diagnosis, 2006, vol. 26, pp. 1216-1218.
Karoui, N.E., et al., "Getting more from digital SNP data," Statist Med, 2006, vol. 25, pp. 3124-3133.
Larrabee, Paige, B., et al., "Microarray Analysis of Cell-Free Fetal DNA in Amniotic Fluid: A Prenatal Molecular Karyotype," Sep. 1, 2004, American Journal of Human Genetics, vol. 75, No. 3, pp. 485-491.
Li, R., et al., "SOAP2: an improved ultrafast tool for short read alignment," Bioinformatics, [online], 2009; vol. 25, No. 15, pp. 1966-1967, [retrieved on Oct. 25, 2012], <URL: http://bioinformatics.oxfordjournals.org/>.
Li, R., et al.,"SOAP: short oligonucleotide alignment program," Bioinformatics, [online], 2008; vol. 24, No. 5, pp. 713-714, [retrieved on Oct. 25, 2012], <URL: http://bioinformatics.oxfordjournals.org/>.
Li, Ying, et al., "Size Separation of Circulatory DNA in Maternal Plasma Permits Ready Detection of Fetal DNA Polymorphisms," Jun. 1, 2004, Clinical Chemistry, American Association for Clinical Chemistry, vol. 50, No. 6, pp. 1002-1011.
Lien, Sigbjorn, et al., "Single-Sperm Tying," Curr Protoc Hum Genet, 2002, Chapter 1, Unit 1.6, 18 pages.
Lo, et al., "Quantitative Analysis of Fetal DNA in Maternal Plasma and Serum: Implications for Noninvasive Prenatal Diagnosis," Am J. Hum Genet, 1998, vol. 62, pp. 768-775.
Lo, Y.M. Dennis, et al., "Digital PCR for the molecular detection of fetal chromosomal aneuploidy," PNAS USA, 2007, vol. 104, pp. 13116-13121.
Lo, Y.M. Dennis, et al., "Direct haplotype determination by double ARMS: specificity, sensitivity and genetic applications," Nucleic Acids Res, 1991; vol. 19, pp. 3561-3567.
Lo, Y.M. Dennis, et al., "Plasma placental RNA allelic ratio permits noninvasive prenatal chromosomal aneuploidy detection," Nature Medicine, 2007; vol. 13, pp. 218-223.
Lo, Y.M. Dennis, et al., "Presence of fetal DNA in maternal plasma and serum," The Lancet, 1997, vol. 350, pp. 485-487.
Lun, Fiona M.F., et al., "Noninvasive prenatal diagnosis of monogenic diseases by digital size selection and relative mutation dosage on DNA in maternal plasma," PNAS USA, 2008, vol. 105, pp. 19920-19925.
Lun, Fiona, M. F., et al.; "Microfluidics Digital PCR Reveals a Higher Than Expected Fraction of Fetal DNA in Maternal Plasma;" Clin Chem, Oct. 1, 2008, vol. 54; No. 10; pp. 1664-1672.
Lun, Fiona M.F., et a., "Epigenetic Analysis of RASSF1A Gene in Cell-Free DNA in Amniotic Fluid," Letter to the Editor, Clinical Chemistry, 2007, vol. 53, No. 4, pp. 796-798.
Margulies, Marcel et al.; "Genome sequencing in microfabricated high-density picolitre reactors"; Nature, Sep. 15, 2005, vol. 437, pp. 376-380.
Majer, Sandra, et al., "Maternal urine for prenatal diagnosis—an analysis of cell-free fetal DNA in maternal urine and plasma in the third trimester," Prenatal Diagnosis, 2007, vol. 27, pp. 1219-1223.
McKernan, K.J., et al., "Sequence and structural variation in a human genome uncovered by short-read, massively parallel ligation sequencing using two-base encoding," Genome Res, [online], 2009; vol. 19, pp. 1527-1541, [retrieved on Oct. 25, 2012], <URL: genome.cshlp.org>.
McLachlan, Geoffrey, et al., "Mixtures with Nonnormal Components," Finite Mixture Models, 2000, pp. 135-174.
McLachlan, Geoffrey, et al., "Multivariate Normal Mixtures," Finite Mixture Models, 2000, pp. 81-116.

(56) References Cited

OTHER PUBLICATIONS

Michalatos-Beloin, Sonia, et al., Molecular haplotyping of genetic markers 10 kb apart by allele-specific long-range PCR, Nucleic Acids Res, 1996; vol. 24, pp. 4841-4843.

Ohtsuka, E., et al., "An Alternative Approach to Deoxyoligonucleotides as Hybridization Probes by Insertion of Deoxyinosine at Ambiguous Codon Positions," J. Biol. Chem., Mar. 10, 1985, vol. 260, pp. 2605-2608.

Pertl, B., et al., "Detection of male and female fetal DNA in maternal plasma by multiplex fluorescent polymerase chain reaction amplification of short tandem repeats," Human Genetics, 2000, vol. 106, pp. 45-49.

Poon, Leo, L. M., et al.; "Differential DNA Methylation between Fetus and Mother as a Strategy for Detecting Fetal DNA in Maternal Plasma"; Clin Chem, 2002, vol. 48, No. 1, pp. 35-41.

Qu, James, Z.Z., et al., "Noninvasive Prenatal Determination of Twin Zygosity by Maternal Plasma DNA Analysis," Clinical Chemistry, 2013, vol. 59, No. 2, pp. 427-435.

Reed, W., et al., "Non-Invasive Determination of the Paternal HLA Haplotype of a Fetus Using Kinetic PCR to Detect Fetal Microchimerism in Maternal Plasma," Mar. 2, 2002, Bone Marrow Transplantation, vol. 29, No. 6, pp. 527-529.

Rossolini, G.M., et al., "Use of deoxyinosine-containing primers vs degenerate primers for polymerase chain reaction based on ambiguous sequence information," Mol. Cell. Probes, 1994, vol. 8, pp. 91-98.

Ruano, Gualberto, et al., "Haplotype of multiple polymorphisms resolved by enzymatic amplification of single DNA moledules," PNAS USA, 1990, vol. 87, pp. 6296-6300.

Saito, Hiroshi, et al., "Prenatal DNA diagnosis of a single-gene disorder from maternal plasma," The Lancet, 2000, vol. 356, p. 1170.

Salem, Rany, M., "A comprehensive literature review of haplotyping software and methods for use with unrelated individuals," Human Genomics, 2005, vol. 2, No. 1, pp. 39-66.

Smid, Maddalena, et al., "Fetal DNA in Maternal Plasma in Twin Pregnancies," Clinical Chemistry, 2003, pp. 1526-1528, vol. 49, No. 9.

Smirnova, Anna, S., et al., "A novel strategy for defining haplotypes by selective depletion using restriction enzymes," Immunogenetics, 2007; vol. 59, pp. 93-98.

Tewhey, R., et al., "Microdroplet-based PCR enrichment for large-scale targeted sequencing," Nat Biotechnol, Nov. 2009, vol. 27, No. 11, pp. 1025-1031.

Tong, Yu, K., et al., "Noninvasive Prenatal Detection of Fetal Trisomy 18 by Epigenetic Allelic Ratio Analysis in Maternal Plasma: Theoretical and Empirical Considerations," Clinical Chemistry, 2006, vol. 52, No. 12, pp. 2194-2202.

Tungwiwat, W., et al., "Non-invasive fetal sex determination using a conventional nested PCR analysis of fetal DNA in maternal plasma," Clinica Chimica Acta, 2003, vol. 334, pp. 173-177.

Wright, Caroline, F., et al., "The use of cell-free fetal nucleic acids in maternal blood for non-invasive prenatal diagnosis," Human Reproductive Update, 2009, vol. 15, No. 1, pp. 139-151.

Xiao, Ming, et al., "Determination of Haplotypes from Single DNA Molecules: A Method for Single-Molecule Barcoding," Human Mutation, 2007, vol. 28, No. 9, pp. 913-921.

Zhou, W., et al., "Counting alleles reveals a connection between chromosome 18q loss and vascular invasion," Nat Biotechnol, Jan. 2001, vol. 19, pp. 78-81.

Non-Final Office Action dated Sep. 28, 2015 in U.S. Appl. No. 13/405,073, filed Feb. 24, 2012. 23 pages.

Extended European Search Report dated Sep. 28, 2016 in EP Patent Application No. 14764129.4. 9 pages.

Curnow, Kirsten J. et al.; "Detection of triploid, molar, and vanishing twin pregnancies by a single-nucleotide polymorphism-based noninvasive prenatal test"; American Journal of Obstetrics & Gynecology; Jan. 2015; vol. 212, Issue 1; pp. 79.e1-79.e9 (9 pages).

* cited by examiner

|  | Mother | | Father | | Type of locus |
|---|---|---|---|---|---|
| | Hap I | Hap II | Hap III | Hap IV | |
| Locus 1 | A | B | A | A | Type α |
| Locus 2 | B | A | A | A | Type β |
| Locus 3 | A | B | A | A | Type α |
| Locus 4 | B | A | A | A | Type β |
| Locus 5 | A | B | A | A | Type α |
| Locus 6 | B | A | A | A | Type β |

*Fig. 3*

Both fetuses have inherited the maternal Hap I

|  | Mother | | Fetus I | | Fetus II | |
|---|---|---|---|---|---|---|
|  | Hap I | Hap II | Hap I | Paternal Hap III/IV | Hap I | Paternal Hap III/IV |
| Locus 1 | A | B | A | A | A | A |
| Locus 2 | B | A | B | A | B | A |
| Locus 3 | A | B | A | A | A | A |
| Locus 4 | B | A | B | A | B | A |
| Locus 5 | A | B | A | A | A | A |
| Locus 6 | B | A | B | A | B | A |

*Fig. 4A*

Both fetuses have inherited Hap I from the mother.

Assuming that each fetus contributes to 10% of total DNA in maternal plasma

|  | Mother (80%) | | Fetus I (10%) | | Fetus II (10%) | |
|---|---|---|---|---|---|---|
|  | Hap I | Hap II | Hap I | III/IV | Hap I | III/IV |
| Type α SNP | A | B | A | A | A | A |
| Type β SNP | B | A | B | A | B | A |

Fractional concentration (F) of the A allele (paternal allele)

| Type α SNP | F = 60% |
|---|---|
| Type β SNP | F = 50% |

*Fig. 4B*

Both fetuses have inherited the maternal Hap II

| | Mother | | Fetus I | | Fetus II | |
|---|---|---|---|---|---|---|
| | Hap I | Hap II | Hap I | Paternal Hap III/IV | Hap I | Paternal Hap III/IV |
| Locus 1 | A | B | B | A | B | A |
| Locus 2 | B | A | A | A | A | A |
| Locus 3 | A | B | B | A | B | A |
| Locus 4 | B | A | A | A | A | A |
| Locus 5 | A | B | B | A | B | A |
| Locus 6 | B | A | A | A | A | A |

*Fig. 5A*

Both fetuses have inherited Hap II from the mother.

Assuming that each fetus contributes to 10% of total DNA in maternal plasma

| | Mother (80%) | | Fetus I (10%) | | Fetus II (10%) | |
|---|---|---|---|---|---|---|
| | Hap I | Hap II | Hap II | Paternal Hap III/IV | Hap II | Paternal Hap III/IV |
| Type α SNP | A | B | B | A | B | A |
| Type β SNP | B | A | A | A | A | A |

Fractional concentration (F) of the A allele (paternal allele)

| Type α SNP | F = 50% |
|---|---|
| Type β SNP | F = 60% |

*Fig. 5B*

One fetus has inherited Hap I and the other has inherited Hap II from the mother

|  | Mother | | Fetus I | | Fetus II | |
|---|---|---|---|---|---|---|
|  | Hap I | Hap II | Hap I | Paternal Hap III/IV | Hap I | Paternal Hap III/IV |
| Locus 1 | A | B | A | A | A | A |
| Locus 2 | B | A | B | A | B | A |
| Locus 3 | A | B | A | A | A | A |
| Locus 4 | B | A | B | A | B | A |
| Locus 5 | A | B | A | A | A | A |
| Locus 6 | B | A | B | A | B | A |

*Fig. 6A*

One fetus has inherited Hap I and the other has inherited Hap II from the mother

Assuming that each fetus contributes to 10% of total DNA in maternal plasma

|  | Mother (80%) | | Fetus I (10%) | | Fetus II (10%) | |
|---|---|---|---|---|---|---|
|  | Hap I | Hap II | Hap I | Paternal Hap III/IV | Hap II | Paternal Hap III/IV |
| Type α SNP | A | B | A | A | B | A |
| Type β SNP | B | A | B | A | A | A |

Fractional concentration (F) of the A allele (paternal allele)

| Type α SNP | F = 55% |
|---|---|
| Type β SNP | F = 55% |

*Fig. 6B*

Fractional concentration of
the shared alleles (A allele) in maternal plasma

| Scenario | Fractional concentration of the A allele by type α SNPs | Fractional concentration of the A allele by type β SNPs | Type α : type β ratio |
|---|---|---|---|
| Both fetuses inherit Hap I | 60% | 50% | 1.2 : 1 |
| Both fetuses inherit Hap II | 50% | 60% | 1 : 1.2 |
| One inherits Hap I and the other inherits Hap II | 55% | 55% | 1 : 1 |

710

Both fetuses have inherited Hap I from the mother.

Assuming that fetus I and II contribute to a% and b% of total DNA in maternal plasma

|  | Mother (100% - a% - b%) | | Fetus I (a%) | | Fetus II (b%) | |
|---|---|---|---|---|---|---|
|  | Hap I | Hap II | Hap I | III/IV | Hap I | III/IV |
| Type α SNP | A | B | A | A | A | A |
| Type β SNP | B | A | B | A | B | A |

Fractional concentration (F) of the A allele (paternal allele)

Type α SNP  $F = \frac{100\% - a\% - b\%}{2} + a\% + b\% = 50\% + \frac{a\% + b\%}{2}$ Type β SNP  $F = 50\%$

*Fig. 10A*

Both fetuses have inherited Hap II from the mother.

Assuming that fetus I and II contribute to a% and b% of total DNA in maternal plasma

|  | Mother (100% - a% - b%) | | Fetus I (a%) | | Fetus II (b%) | |
|---|---|---|---|---|---|---|
|  | Hap I | Hap II | Hap II | Paternal Hap III/IV | Hap II | Paternal Hap III/IV |
| Type α SNP | A | B | B | A | B | A |
| Type β SNP | B | A | A | A | A | A |

Fractional concentration (F) of the A allele (paternal allele)

Type α SNP  $F = 50\%$

Type β SNP  $F = \frac{100\% - a\% - b\%}{2} + a\% + b\% = 50\% + \frac{a\% + b\%}{2}$

*Fig. 10B*

One fetus has inherited Hap I and the other has inherited Hap II from the mother

Assuming that fetus I and II contribute to a% and b% of total DNA in maternal plasma

|  | Mother (100% - a% - b%) | | Fetus I (a%) | | Fetus II (b%) | |
|---|---|---|---|---|---|---|
|  | Hap I | Hap II | Hap I | Paternal Hap III/IV | Hap II | Paternal Hap III/IV |
| Type α SNP | A | B | A | A | B | A |
| Type β SNP | B | A | B | A | A | A |

Fractional concentration (F) of the A allele (paternal allele)

Type α SNP $\quad F = \frac{100\% - a\% - b\%}{2} + a\% + \frac{b\%}{2} = 50\% + \frac{a\%}{2}$ Type β SNP $\quad F = \frac{100\% - a\% - b\%}{2} + \frac{a\%}{2} + b\% = 50\% + \frac{b\%}{2}$

*Fig. 11A*

Fractional concentration of the shared alleles (A allele) in maternal plasma 1150

| Scenario | Fractional concentration of the A allele by type α SNPs | Fractional concentration of the A allele by type β SNPs | Type α : type β ratio |
|---|---|---|---|
| Both fetuses inherit Hap I | $50\% + \frac{a\% + b\%}{2}$ | 50% | $(1 + a\% + b\%) : 1$ |
| Both fetuses inherit Hap II | 50% | $50\% + \frac{a\% + b\%}{2}$ | $1 : (1 + a\% + b\%)$ |
| One inherits Hap I and the other inherits Hap II | $50\% + \frac{a\%}{2}$ | $50\% + \frac{b\%}{2}$ | $(50\% + \frac{a\%}{2}) : (50\% + \frac{b\%}{2})$ |

Table 1500. RHDO analysis for the maternal haplotype inheritance for Case 1.

| Classification block | No. of each of the type α and type β SNP loci in the classification block | Type α SNPs ||| Type β SNPs ||| α/β ratio | Fetal inheritance |
|---|---|---|---|---|---|---|---|---|---|
| | | Total no. of counts of the shared alleles | Total no. of counts of the non-paternal alleles | Fractional concentration of the shared alleles | Total no. of counts of the shared alleles | Total no. of counts of the non-paternal alleles | Fractional concentration of the shared alleles | | |
| 1 | 15 | 3609 | 2782 | 0.564 | 2965 | 2172 | 0.577 | 0.978 | Hap I/Hap II |
| 2 | 12 | 2840 | 2562 | 0.525 | 3132 | 1966 | 0.614 | 0.855 | Hap I/Hap II |
| 3 | 16 | 3360 | 2428 | 0.580 | 2881 | 2194 | 0.567 | 1.023 | Hap I/Hap II |
| 4 | 15 | 3034 | 2486 | 0.549 | 3109 | 2418 | 0.562 | 0.977 | Hap I/Hap II |
| 5 | 17 | 4503 | 3555 | 0.558 | 2829 | 2346 | 0.546 | 1.022 | Hap I/Hap II |
| 6 | 11 | 3173 | 2400 | 0.569 | 2739 | 2308 | 0.542 | 1.049 | Hap I/Hap II |
| 7 | 18 | 4452 | 3503 | 0.559 | 2809 | 2377 | 0.541 | 1.033 | Hap I/Hap II |
| 8 | 20 | 5770 | 4166 | 0.580 | 2924 | 2562 | 0.532 | 1.089 | Hap I/Hap II |
| 9 | 18 | 3209 | 2507 | 0.561 | 4589 | 3425 | 0.572 | 0.980 | Hap I/Hap II |

Fig. 15

Table 1600. RHDO analysis for the maternal haplotype inheritance for Case 2.

| Classification block | No. of each of the type α and type β SNP loci in the classification block | Type α SNPs | | | Type β SNPs | | | α/β ratio | Fetal inheritance |
|---|---|---|---|---|---|---|---|---|---|
| | | Total no. of counts of the shared alleles | Total no. of counts of the non-paternal alleles | Fractional concentration of the shared alleles | Total no. of counts of the shared alleles | Total no. of counts of the non-paternal alleles | Fractional concentration of the shared alleles | | |
| 1 | 13 | 3963 | 1813 | 0.686 | 2815 | 2515 | 0.528 | 1.299 | Hap I/Hap I |
| 2 | 15 | 3148 | 1869 | 0.627 | 2790 | 2621 | 0.515 | 1.217 | Hap I/Hap I |
| 3 | 18 | 3571 | 1988 | 0.642 | 2754 | 2618 | 0.512 | 1.253 | Hap I/Hap I |
| 4 | 22 | 6281 | 3127 | 0.667 | 2659 | 2653 | 0.500 | 1.333 | Hap I/Hap I |
| 5 | 20 | 3998 | 2161 | 0.649 | 2692 | 2662 | 0.502 | 1.291 | Hap I/Hap I |
| 6 | 19 | 4523 | 2040 | 0.689 | 2517 | 2495 | 0.502 | 1.372 | Hap I/Hap I |
| 7 | 17 | 4268 | 2221 | 0.657 | 2810 | 2647 | 0.514 | 1.277 | Hap I/Hap I |
| 8 | 20 | 3310 | 1717 | 0.658 | 3652 | 3546 | 0.507 | 1.298 | Hap I/Hap I |
| 9 | 18 | 3704 | 2257 | 0.621 | 2638 | 2558 | 0.507 | 1.224 | Hap I/Hap I |

Fig. 16

DETERMINING FETAL GENOMES FOR MULTIPLE FETUS PREGNANCIES

CROSS REFERENCE TO RELATED APPLICATIONS

The present application claims priority from U.S. Provisional Application No. 61/789,992, entitled "Determining Fetal Genomes For Multiple Fetus Pregnancies" filed Mar. 15, 2013, the entire contents of which are herein incorporated by reference for all purposes.

This application is related to commonly owned U.S. Patent Publication No. 2011/0105353 entitled "Fetal Genomic Analysis From A Maternal Biological Sample" by Lo et al.; and U.S. Patent Publication No. US 2013/0059733 entitled "Molecular Testing Of Multiple Pregnancies" by Lo et al., the disclosures of which are incorporated by reference in its entirety.

FIELD

The present invention relates generally to analyzing a fetal genome based on a maternal sample, and more particularly to determining all or parts of fetal genomes of a multiple fetus pregnancy based on an analysis of genetic fragments in the maternal sample.

BACKGROUND

The discovery of cell-free fetal nucleic acids in maternal plasma in 1997 opened up new possibilities for noninvasive prenatal diagnosis (Lo Y M D et al Lancet 1997; 350: 485-487; and U.S. Pat. No. 6,258,540). This technology has been rapidly translated to clinical applications, with the detection of fetal-derived, paternally-inherited genes or sequences, e.g. for fetal sex determination, fetal RhD status determination, and determination of whether the fetus has inherited a paternally-inherited mutation (Amicucci P et al Clin Chem 2000; 46: 301-302; Saito H et al Lancet 2000; 356: 1170; and Chiu R W K et al Lancet 2002; 360: 998-1000). Recent progress in the field has enabled the prenatal diagnosis of fetal chromosomal aneuploidies, such as trisomy 21, from maternal plasma nucleic acid analysis (Lo Y M D et al Nat Med 2007; 13: 218-223; Tong Y K et al Clin Chem 2006; 52: 2194-2202; US Patent publication 2006/0252071; Lo Y M D et al Proc Natl Acad Sci USA 2007; 104: 13116-13121; Chiu R W K et al Proc Natl Acad Sci USA 2008; 105: 20458-20463; Fan H C et al Proc Natl Acad Sci 2008; 105: 16266-16271; US Patent publication 2007/0202525; and US Patent publication 2009/0029377).

Another area of significant recent progress is the use of single molecule counting methods, such as digital PCR, for the noninvasive prenatal diagnosis of single gene diseases in which the mother and father both carry the same mutation. This has been achieved by relative mutation dosage (RMD) analysis in maternal plasma (US Patent application 2009/0087847; Lun F M F et al Proc Natl Acad Sci USA 2008; 105: 19920-19925; and Chiu R W K et al. Trends Genet 2009; 25: 324-331).

However, such methods use prior knowledge of possible mutations to analyze specific parts of a genome, and thus may not identify latent or uncommon mutations or genetic diseases. Further, information concerning the zygosity of twin pregnancies has conventionally been obtained by ultrasound scanning (Chauhan S P et al. *Am J Obstet Gynecol* 2010; 203: 305-315) or invasive prenatal diagnosis (e.g. amniocentesis) (Chen C P et al. *Hum Reprod* 2000; 15: 929-934).

Therefore, it is desirable to provide new methods, systems, and apparatus that can identify all or parts of fetal genomes of a multiple fetus pregnancy using non-invasive techniques.

SUMMARY

Embodiments of the invention provide methods, systems, and apparatuses for determining inheritance of maternal and paternal haplotypes in preganncies with multiple fetuses. Maternal inheritance can be determined at loci where the mother is heterozygous and the paternally inherited alleles are known (e.g., the father is homozygous). Two types of loci may be used, where one type has the paternal allele appear on a first maternal haplotype, and another type has the paternal allele appear on a second maternal haplotype. Paternal inheritance can be determined from loci where the father is heterozygous and the maother is homozygous. Amounts of different alleles at each locus can be measured. A comparison of the amounts (e.g., using a fractional concentration of each allele and cutoffs) can be used to determine the haplotype inheritance. A haplotype can be linked to a condition of interest.

Some embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 3 shows the haplotypes of a hypothetical father and mother with identifications of two types of loci according to embodiments of the present invention.

FIG. 4A shows an example where both fetuses have inherited Hap I from the mother for the loci shown in FIG. 3. FIG. 4B shows an example calculation of the fractional concentration of the allele shared by the father and mother (A allele) in maternal plasma when both fetuses have inherited Hap I from the mother.

FIG. 5A shows an example where both fetuses have inherited Hap II from the mother for the loci shown in FIG. 3. FIG. 5B shows an example calculation of the fractional concentration of the allele shared by the father and mother (A allele) in maternal plasma when both fetuses have inherited Hap II from the mother.

FIG. 6A shows an example where one fetus has inherited Hap I and one has inherited Hap II from the mother for the loci shown in FIG. 3. FIG. 6B shows an example calculation of the fractional concentration of the allele shared by the father and mother (A allele) in maternal plasma when one fetus has inherited Hap I and the other fetus has inherited Hap II from the mother.

FIG. 10A shows the fractional concentrations of the shared allele (A allele) in the maternal plasma for type α and type β SNPs when both fetuses have inherited Hap I from the mother and the fetuses contribute different fetal DNA percentages.

FIG. 10B shows the fractional concentrations of the shared allele (A allele) in the maternal plasma for type α and type β SNPs when both fetuses have inherited Hap II from the mother when the fetuses contribute different fetal DNA percentages FIG. 11A shows the fractional concentrations of the shared allele (A allele) in the maternal plasma for Type α and Type β SNPs when one fetus inherits Hap I and the other fetus inherits Hap II from the mother when the fetuses contribute different fetal DNA percentages.

FIG. 11B shows a table 1150 of the fractional concentrations of A alleles using type α and β SNPs and the ratio of these two concentrations in the three scenarios.

FIG. 15 is a table 1500 showing the RHDO analysis of a chromosomal segment on the long arm of chromosome 4 for Case 1.

FIG. 16 is a table 1600 showing the RHDO analysis of a chromosomal segment on the long arm of chromosome 4 for Case 2.

DEFINITIONS

Figure 1:
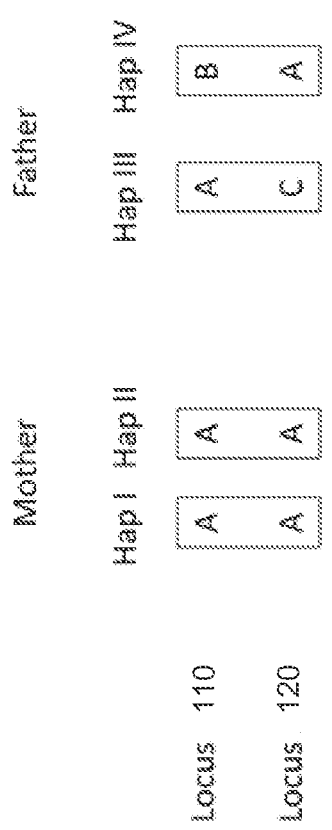
FIG. 1 shows an example of two loci where the mother is homozygous and the father is heterozygous according to embodiments of the present invention.

The term "biological sample" as used in this disclosure refers to any sample that is taken from a subject (for example, a human, such as a pregnant woman) and contains one or more nucleic acid molecule(s) of interest. Samples useful in the practice of this invention include plasma, serum, blood cells, leukocytes, reticulocytes, and whole blood. For some purposes, saliva, pleural fluid, sweat, ascitic fluid, bile, urine, pancreatic juice, stool or cervical smear samples may also be used.

The term "locus" or its plural form "loci" is a location or address of any length of nucleotides (or base pairs) which has a variation across genomes.

As used herein, the term "locus" or its plural form "loci" is a location or address of any length of nucleotides (or base pairs) which has a variation across genomes. The term "alleles" refers to alternative DNA sequences at the same physical genomic locus, which may or may not result in different phenotypic traits. In any particular diploid organism, with two copies of each chromosome (except the sex chromosomes in a male human subject), the genotype for each gene comprises the pair of alleles present at that locus, which are the same in homozygotes and different in heterozygotes. A population or species of an organism typically includes multiple alleles at each locus among various individuals. A genomic locus where more than one allele is found in the population is termed a polymorphic site. Allelic variation at a locus is measurable as the number of alleles (i.e., the degree of polymorphism) present, or the proportion of heterozygotes (i.e., the heterozygosity rate) in the population. The presence or absence of a sequence (e.g. a gene) is also considered to be a type of allelic variation, as a locus can include the sequence or not include the sequence. Such an absence of a sequence (e.g. the RHD gene) can be identified, for example, by the junction of the sequences that normally come before and after the deleted sequence. As used herein, the term "polymorphism" refers to any inter-individual variation in the human genome, regardless of its frequency. Examples of such variations include, but are not limited to, single nucleotide polymorphisms, simple tandem repeat polymorphisms, insertion-deletion polymorphisms, mutations (which may be disease causing) and copy number variations.

The term "haplotype" refers to a combination of alleles at multiple loci that are transmitted together on the same chromosome or chromosomal region. A haplotype may refer to as few as one pair of loci or to a chromosomal region, or to an entire chromosome.

A "chromosomal region" refers to a plurality of nucleotide positions for a particular chromosome. The chromosomal region may be an entire chromosome or a smaller subsection. In a normal person, a chromosomal region will have two haplotypes, one for each copy of the chromosome that the region is within. The two haplotypes may be the same or different in the chromosomal region.

The term "cutoff value" or amount as used in this disclosure means a numerical value or amount that is used to arbitrate between two or more states of classification for a biological sample—for example, the presence or absence of a genetic sequence that is associated or linked with a particular phenotypic condition or disease, or a susceptibility to a phenotypic condition or disease. For example, if a parameter is greater than the cutoff value, a first classification of the quantitative data is made, or if the parameter is less than the cutoff value, a different classification of the quantitative data is made.

DETAILED DESCRIPTION

Embodiments can determine determining inheritance of maternal and paternal haplotypes in pregnancies with multiple fetuses. Paternal inheritance can be determined from loci where the father is heterozygous and the mother is homozygous. An amount of the paternal-specific alleles (e.g., a fractional concentration of those alleles) can be used to determine how many fetuses have inherited a haplotype with the paternal-specific alleles. Knowledge of the paternally-inherited haplotypes in the fetuses can be used in determining the maternal haplotypes inherited by the fetuses.

Maternal inheritance can be determined at loci where the mother is heterozygous and the paternally inherited alleles are known (e.g., the father is homozygous or paternally-inherited haplotype is determined). Two types of loci may be used. One type has the paternal allele appear on a first maternal haplotype, and another type has the paternal allele appears on a second maternal haplotype. Amounts of different alleles at each locus can be measured. A comparison of the amounts (e.g., using a fractional concentration of each allele and cutoffs) can be used to determine the haplotype inheritance. And, a haplotype can be linked to a condition of interest, which can be determined to be inherited or not inherited based on the determination of which paternal and/or maternal haplotypes are inherited.

I. Zygosity

Multiple pregnancy refers to a pregnancy in which more than one fetus is carried by a pregnant woman. Twin pregnancies are the most common form of multiple pregnancies. A twin pregnancy can be characterized as monozygotic (identical) and dizygotic (not identical). Although the discussion is mainly focused on twins, aspects are also applicable to higher numbers of fetuses.

Analysis of DNA fragments present in maternal plasma is more complicated in twin pregnancies—especially if the twins are dizygotic (not identical). Even if a particular haplotype or a particular disease-linked polymorphism is identified in the maternal plasma as fetal in origin, the analyst is faced with another problem: how to determine whether both of the fetuses are affected, or only one.

A. Monozygotic Twins

When a pregnant woman carries a pair of monozygotic twins, the genetic analysis for the fetuses can be similar to that used for analyzing singleton pregnancies. But, the possibility of dizygotic twins makes the analysis more difficult. For the analysis of paternal inheritance, a paternal allele that is absent in the maternal genome can be used as a marker to determine which paternal allele is inherited by the fetuses. When the paternal allele is known to be on a particular haplotype of the father, an inheritance of the particular haplotype by at least one of the fetuses can be determined (by both when monozygotic).

For the analysis of the inheritance of maternal alleles, complex quantitative approaches are required because the two maternal alleles would be detectable in the maternal plasma regardless of which maternal allele is inherited by the fetuses. The relative amounts of the two maternal alleles in maternal plasma can be compared, and the allele inherited by the fetus is expected to be present at a higher concentration. In another embodiment, the relative amounts of the two maternal haplotypes in maternal plasma are compared. This relative haplotype dosage approach could provide more accurate result when the amount of DNA in the plasma sample is limiting. Details about a relative haplotype dosage approach can be found in U.S. Pat. No. 8,467,976, which is incorporated by reference.

B. Dizygotic Twins

If the pair of twins are dizygotic, the two fetuses may inherit same or different alleles from each of the parents. In this scenario, more complex genetic analysis is required to determine which paternal and maternal alleles are inherited by each fetus. This information is useful for the analysis of monogenic diseases and other conditions.

Embodiments describe techniques for analyzing the inheritance of parental haplotypes by the fetuses in a multiple fetus pregnancy. The analysis is divided into the analysis of paternal inheritance, and analysis of the maternal inheritance.

II. Analysis for Paternal Inheritance

The determination of which paternal haplotype(s) is inherited by the fetuses can be performed when a genotype and/or haplotype information is known about the father. Some embodiments provide a method for determining parental inheritance by identifying and measuring parental-specific haplotypes.

A. Identification of Paternal Specific Haplotypes

A determination of paternal inheritance can be performed by analyzing loci where the mother is homozygous and the father is heterozygous. In such instances, a fetal-specific allele can be inherited from the father in either or both fetuses.

FIG. 1 shows an example of two loci where the mother is homozygous and the father is heterozygous according to embodiments of the present invention. These two loci 110, 120 are close to each other so that recombination between these two loci during a single meiosis is unlikely. In this example, at locus 110, the paternal A allele is the same as the maternal alleles and the paternal B allele is absent in the mother and, hence, is paternal-specific. Similarly, the C allele at locus 120 is also paternal-specific.

In one embodiment, the phase of the paternal-specific alleles at the two different loci can be determined. The phase of the alleles refers to the relationship of these alleles with regard to whether they are on the same chromosome or on different homologous chromosomes. The alleles at different loci located on the same chromosome form a haplotype. Increasing the number of specific loci analyzed on each paternal haplotype can increase the sensitivity of detecting the paternal-specific alleles in the maternal plasma, as more paternal-specific alleles can be detected. The increase in the number of paternal-specific alleles detected increases the accuracy of deducing the paternal inheritance of the fetuses.

The maternal plasma DNA is then analyzed for the paternal-specific alleles of these two loci. Different techniques can be used for the detecting these paternal-specific alleles in the maternal plasma and these methods would be known to those skilled-in-the-art. Examples of these methods include, but not limited to, polymerase chain reaction (PCR), digital PCR, allele-specific PCR, DNA sequencing, primer extension reaction, mass-spectrometry-based methods and next-generation sequencing.

For determining if the two fetuses inherit the same paternal haplotype, at least one paternal-specific allele for each of the two paternal haplotypes can be analyzed. FIG. 1 shows two paternal haplotypes Hap II and Hap IV. In the example, if the B allele is detected in the maternal plasma for locus 110, it implies that the paternal haplotype Hap IV is inherited by at least one of the fetuses. Similarly, if the C allele is detected in the maternal plasma for locus 120, the paternal Hap III is inherited by at least one of the fetuses. In twin pregnancy, the presence of paternal-specific alleles located on each of the two paternal haplotypes in maternal plasma indicates that the two fetuses have inherited different paternal haplotypes. If only the paternal-specific allele at locus 110 (B allele) is present in the maternal plasma but the paternal-specific allele at locus 120 (C allele) is absent, both fetuses have inherited the paternal Hap IV. Similarly, if only the paternal-specific allele at locus 120 (C allele) is present in the maternal plasma but the paternal-specific allele at locus 110 (B allele) is absent, both fetuses have inherited the paternal Hap III.

The detectability of the paternal-specific alleles on a paternal haplotype in maternal plasma can be affected by the fractional concentration of DNA contributed by each fetus, and the sensitivity of detecting each paternal-specific allele. In the presence of a low fractional fetal DNA concentration, even when a fetus has inherited a paternal-specific allele, the allele may not be detected in the maternal plasma. To reduce the chance of falsely concluding that a paternal haplotype is not inherited by the fetus, a larger the number of paternal-specific alleles on a paternal haplotype can be analyzed.

B. Method for Determining Paternal Inheritance

Figure 2:
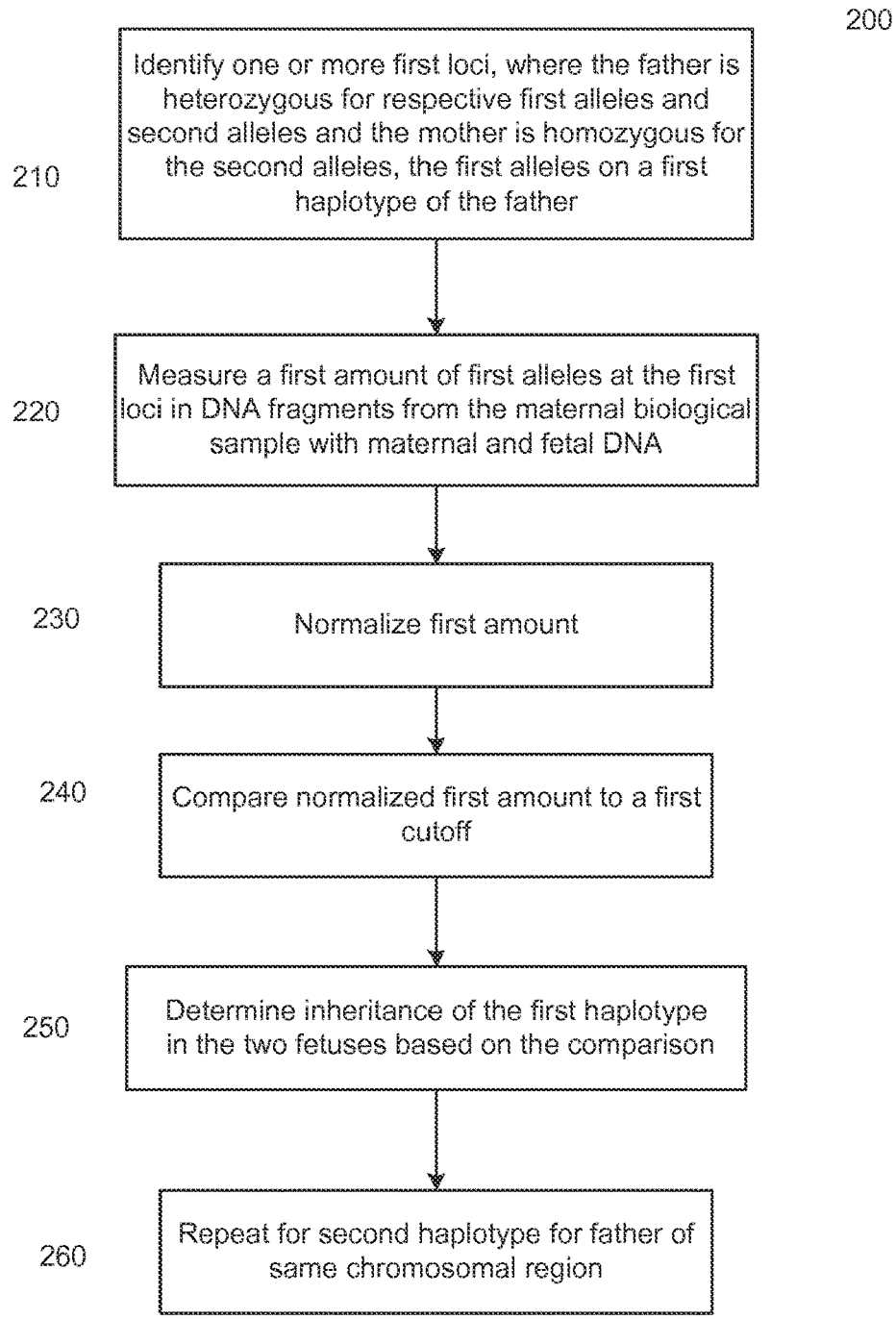
FIG. 2 is a flowchart of a method 200 for determining inheritance of partneranl haplotypes in fetuses of a multiple fetus pregnancy according to embodiments of the present invention.

FIG. 2 is a flowchart of a method 200 for determining inheritance of paternal haplotypes in fetuses of a multiple fetus pregnancy according to embodiments of the present invention. Embodiments can analyze paternal inheritance in dizygotic twin fetuses. Method 200 can use a biological sample that is obtained from a female pregnant with more than one fetus. The biological sample includes cell-free DNA of the female and the two fetuses. Often used is a blood related sample, such as plasma, serum, blood cells, leukocytes, reticulocytes, or whole blood. Other sample types include urine, saliva, vaginal fluid, washings from the female genital tract, tears and sweat.

The biological sample can be analyzed in various ways, e.g., using digital PCR, sequencing, or other suitable techniques. The analysis can provide a count of a number of alleles at certain loci in a genome. For example, a sequence read can be aligned to a reference genome and the allele in the sequence read can be saved in memory. In another embodiment, a PCR signal can indicate a number of wells (or an amount in a particular well with RT-PCR) that include a DNA fragment corresponding to a labeled probe for a particular locus and allele. Method 200 can be performed by a computer system.

At block 210, a first group of one or more first loci on a first chromosome are identified. At each locus, and the father is heterozygous for a first allele and a second allele, and the mother is homozygous for a first allele. The first alleles are on a first haplotype of a first chromosomal region (e.g., entire chromosome or just part). A second paternal haplotype has the second alleles.

The mother can be genotyped in a variety of ways, as will be known to one skilled in the art. For example, DNA from maternal cells can be analyzed, and loci where only one allele is detected can be identified as homozygous.

The first haplotype of the father can be determined in a variety of ways. In one embodiment, the father can be genotyped and a haplotype can be determined based on a reference haplotype, which may be determined from a particular population to which the father corresponds (e.g., a reference determined for a particular ethnic group). In another embodiment, a biological sample of the father can be analyzed to determine the first haplotype.

At block 220, a first amount of the respective first alleles that are present at the first loci in DNA fragments of the biological sample is measured. As mentioned above, the second amount can be determined by a computer that receives sequence reads or PCR reads (e.g., color signals for a number of wells). The computer can determine a number of DNA fragments that correspond to a particular first locus and count a number of such DNA fragments that have the second allele (e.g., number of wells that have a particular color or a number of aligned sequence reads that have the second allele).

In some embodiments, the analysis is done computationally using sequence data already obtained. A choice of suitable technologies includes what is provided in US 2011/0105353 A1 and US 2013/0059733 A1. As an alternative to sequencing through each locus, the user may test for a particular allele using specific probes or PCR primers. The measuring can be "selective" in the sense that the actual physical sequencing steps and/or the sequence data obtained therefrom is masked, filtered, or otherwise selected to obtain reads that are at or around the haplotype of interest and/or the alleles to which the haplotype is linked.

At block 230, the first amount is optionally normalized. In other embodiments, the first amount is not normalized. In one embodiment, the first amount is normalized by dividing by a second amount of the second alleles at the first loci. In another embodiment, the normalization can be performed by dividing the first amount by a total amount of DNA fragments at the first loci. The result can provide a fractional concentration of the first alleles.

The fractional concentration of the alleles at each locus is then calculated as the count of each of the alleles separately divided by the count of all alleles together. Increasing the number of reads of the biological (maternal) sample increases accuracy of the assessment. Each locus may be analyzed separately and the results combined for consensus. Alternatively, counts of alleles at all of the loci are summed together according to whether they are linked to the first haplotype.

At block 240, the normalized first amount is compared to a first cutoff value. In one embodiment, where the raw value for the first amount is used, the first cutoff may be zero (or other relatively small non-normalized value) such that any detection of a first allele can indicate the existence of the first haplotype in the maternal sample. This analysis may be more qualitative in nature since only the existence of the first haplotype is assumed based on the existence of some first alleles without knowing a percentage or other normalized value for the first allele. And, whether both fetuses have inherited the first allele is not known.

In other embodiments, a higher cutoff can be set so as to avoid spurious data that may cause false positives when the detection of one or more first alleles may be incorrect, e.g., due to errors in the biochemical process used (e.g., sequencing or PCR).

At block 250, the inheritance of the first haplotype is determined based on the comparison. As mentioned above, the determination may be that at least one of the fetuses has inherited the first haplotype when the first amount or the normalized first amount exceeds the first cutoff.

In some embodiments, more than one cutoff can be used. Such examples can be when a fractional concentration of the first allele is determined. If a total fetal DNA percentage in the biological sample is known and/or the individual. This quantitative measurement allows the determination of whether one fetus or both fetuses have the haplotype of interest.

For example, both fetuses can be identified as having inherited the haplotype if the fractional concentration is above the first cutoff value. Both fetuses are identified as not having inherited the haplotype if the fractional concentration is not significantly greater than zero (e.g., less than a second cutoff). If the fractional concentration is not above the first cutoff but is greater than the second cutoff, then one of the fetuses can be determined as has inheriting the first haplotype and the other has not.

In one specific example, assume that the total fetal DNA percentage is 10%, with each fetus contributing 5%. The first cutoff can be between 7-9%, or any suitable percentage that can discriminate between 5% and 10%, given statistical accuracy of the measurement. The second cutoff can be between 2-4%, or any suitable percentage that can discriminate between 0% and 5%, given statistical accuracy of the measurement. In some embodiments, the individual DNA percentage contributed by each fetus may not be known, but a typical range can be assumed based on measurements of other samples. Thus, cutoffs can still be determined in such cases.

The cutoffs used in this analysis can be determined from the relative amount or percentage of DNA from each fetus in the maternal sample. The cutoffs can discriminate between no contribution of the allele from either fetus, contribution from one fetus, or contribution from both fetuses. Further details are provided in to US 2011/0105353 A1 and US 2013/0059733 A1 for more information on setting the cutoff values for each patient or for a population as a whole.

At block 260, blocks 210-250 can be repeated for a second haplotype of the first chromosomal region. For example, one or more second loci can be identified, such as locus 120 that have a paternal-specific allele on the second haplotype (Hap III in FIG. 1). The determination can be made as to whether at least one of the fetuses have inherited the second haplotype. Thus, this determination can be combined with the determination of inheritance for the first haplotype. If both haplotypes are determine to be inherited, then one fetus inherits one of the haplotypes. If only one haplotype is determined to be inherited, then both fetuses can be determined to inherit the same haplotype. Therefore, a determination about inheritance can be made for both fetuses.

If a fractional concentration is determined and used for the first haplotype, then a fractional concentration of the second haplotype can be used to confirm the determined inheritance from the fractional concentration and threshold for the first loci.

As the inherited paternal haplotype(s) is determined, an inherited allele at loci where the mother is heterozygous can be determined. This information about a paternally-inherited allele can be used in determining the inheritance of the maternal haplotypes for the fetuses.

C. Identifying Loci

The data for the parental genomes can be obtained before, during, or after analysis of the biological sample containing the mixture of maternal and fetal DNA. The paternal genome sequence can be obtained by sequencing a biological sample from the male patent. The maternal genome sequence can be obtained by sequencing another biological sample taken before the pregnancy, or from a biological sample that contains essentially no fetal DNA, such as exsanguinated tissue or hair follicles. Alternatively, relevant parts of the genome of the male parent and/or the female parent may be deduced by quantitative assessment of the maternal plasma or sample taken during pregnancy.

In some embodiments, the genotype information for either parent can then be extended into haplotype information of the parents by comparison with the genotype information from other family members, for example, a sibling of the fetus of the current pregnancy, or from the genotypes of the grandparents, etc. Haplotypes of the parents can also be constructed by other methods well known to those skilled in the art. Examples of such methods include methods based on single molecule analysis such as digital PCR (Ding C and Cantor C R. Proc Natl Acad Sci USA 2003; 100: 7449-7453; Ruano G et al. Proc Natl Acad Sci USA 1990; 87: 6296-6300), sperm haplotyping (Lien S et al. Curr Protoc Hum Genet 2002; Chapter 1:Unit 1.6) and imaging techniques (Xiao M et al. Hum Mutat 2007; 28: 913-921). Other methods include those based on allele-specific PCR (Michalatos-Beloin S et al. Nucleic Acids Res 1996; 24: 4841-4843; Lo Y M D et al. Nucleic Acids Res 1991; Nucleic Acids Res 19: 3561-3567), cloning and restriction enzyme digestion (Smirnova A S et al. Immunogenetics 2007; 59: 93-8), etc. Yet other methods are based on the distribution and linkage disequilibirum structure of haplotype blocks in the population which allow the maternal haplotype to be inferred from statistical assessments (Clark A G. Mol Biol Evol 1990; 7:111-22; 10:13-9; Salem R M et al. Hum Genomics 2005; 2:39-66).

The loci for analysis can also be selected on the basis of their proximity to a particular region, e.g., a region where a haplotype is known or where a genetic feature of interest exists. Thus, the loci within the region where the haplotype is known can be selected. Loci that are close to each other can be linked to the same haplotype, and will segregate with the haplotype as long as there has not been a chromosomal cross-over in between them. The user has the choice of enlarging or reducing the region of the chromosome being analyzed. Enlarging the region increases precision of the analysis, because more of the DNA in the maternal sample will be relevant. However, enlarging the region also risks the occurrence of a cross-over event in between, in which case inheritance of an allele cannot accurately predict inheritance of the haplotype.

In one embodiment, a locus to be analyzed is a disease-causing gene. In this scenario, the two paternal alleles of interest may be a disease-causing mutation and a non-disease-causing allele. In another embodiment, the locus to be analyzed is a polymorphism linked to a gene involved in a genetic disease. In this case, the two paternal alleles of interest would be an allele linked to the mutant gene and another allele linked to the normal (i.e. non-mutant) gene.

D. Clinical Assessment

Paternally-inherited autosomal dominant conditions can be evaluated by locating which paternal haplotype is associated with the genetically inheritable condition. This can be done, for example, using digital PCR, chromosome sorting, family study and deduction from population haplotype information. The paternal specific disease linked to a particular haplotype can be then identified the maternal plasma. The presence in the maternal sample (e.g., maternal plasma) of the paternal-specific alleles located on the haplotype of interest can indicate one or both of the fetuses have inherited the condition.

Autosomal recessive conditions can be assessed by determining if one of the fetuses has inherited the paternal haplotype by identifying alleles located on the same paternal haplotype in the maternal plasma. The detection of disease-linked alleles can indicate that at least one fetus has inherited the disease-associated paternal haplotype. Thus, the one or more of the first alleles and/or one or more of the second alleles is linked to a phenotype of interest. And, the phenotype of interest can be a disease or disease susceptibility.

III. Analysis for Maternal Inheritance

The analysis of maternal inheritance for multiple fetuses in a pregnancy is complex because DNA of maternal origin constitutes most of the DNA in the plasma of the mother. DNA of fetal origin represents a small fraction (e.g., of the order of 10 percent), which is a combination of DNA from both of the fetuses in a twin pregnancy. Accordingly, a quantitative approach is used to distinguish and characterize the fetal DNA, as described below.

A. Relative Haplotype Dosage (RHDO) Analysis

For RHDO analysis, one embodiment of the invention is to focus on the category of loci that the mother is heterozygous and the father is homozygous. This eliminates the necessity of having to analyze both maternal and paternal alleles at the same time. SNPs that are homozygous are thus defined as informative for RHDO analysis.

FIG. 3 shows the haplotypes of a hypothetical father and mother with identifications of two types of loci according to embodiments of the present invention. Only the loci where the mother is heterozygous and the father is homozygous are shown. In this illustration, two alleles (e.g. single nucleotide polymorphisms (SNP)) are identified for these informative loci. Other types of polymorphisms, for example microsatellite polymorphisms, can also be used. Although parts of the discussion may refer to SNPs, other types of polymorphisms (variations) may be used.

As part of the RHDO analysis, the SNPs can be divided into two types, type $\alpha$ and type $\beta$. A type $\alpha$ SNP is a SNP locus at which the paternal alleles are identical to the maternal alleles located on Hap I, and a type $\beta$ SNP is a SNP locus at which the paternal alleles are identical to the maternal alleles located on Hap II. As the assignment of Hap I and Hap II is arbitrary, Hap I and Hap II can be defined interchangeably before the analysis.

In this example, Hap III and Hap IV are identical since the father is homozygous at the loci. However, in other embodiments, the father is not homozygous, but a paternally-inherited allele is known, e.g., by determining an inherited paternal haplotype.

In a dizygotic twin pregnancy, there are three possibilities for the inheritance of maternal haplotypes:

Both fetuses have inherited Hap I from the mother (FIG. 4A);
Both fetuses have inherited Hap II from the mother (FIG. 5A);
One fetus has inherited Hap I and one has inherited Hap II from the mother (FIG. 6A).

FIG. 4A shows the haplotypes of the mother and father, which are the same as in FIG. 3. Both fetuses are shown to have inherited Hap I from the mother. The other haplotype of each fetus corresponds to either Hap III or Hap IV, as both are equivalent at the loci shown.

FIG. 4B shows an example calculation of the fractional concentration of the allele shared by the father and mother (A allele) in maternal plasma when both fetuses have inherited Hap I from the mother. Assume that each fetus contributes to 10% of total DNA in the maternal plasma and the mother contributes 80% of the total plasma DNA. For Type $\alpha$ SNPs, the B allele is only present in the maternal genome. Therefore, the fractional concentration of the B allele in the maternal plasma is 40% and the fractional concentration of the A allele (the shared allele between the mother and the father) is 60%. For Type $\beta$ SNP, both fetuses and the mother are heterozygous for the A and B alleles. Therefore the fractional concentration of the A allele in the maternal plasma is 50%.

FIG. 5B shows an example calculation of the fractional concentration of the allele shared by the father and mother (A allele) in maternal plasma when both fetuses have inherited Hap II from the mother. Each fetus is assumed to contribute 10% of total DNA in the maternal plasma, and the mother contributes 80%. For Type $\alpha$ SNPs, both fetuses and the mother are heterozygous for the A and B alleles. Therefore, the fractional concentrations of both the A allele and the B allele in the maternal plasma are 50%. For Type $\beta$ SNP, the B allele is only present in the maternal genome but not in the fetuses. Therefore, the fractional concentration of the B allele in the maternal plasma is 40% and the fractional concentration of the A allele is 60%.

FIG. 6B shows an example calculation of the fractional concentration of the allele shared by the father and mother (A allele) in maternal plasma when one fetus has inherited Hap I and the other fetus has inherited Hap II from the mother. Assuming that each fetus contributes 10% of total DNA in the maternal plasma and the mother contributes 80% of the total plasma DNA, the fractional concentration of the A allele would be 55% for both Type $\alpha$ and Type $\beta$ SNPs.

B. Comparison of the Predicted Values with Actual Fractional Concentration

The examples above assumed a particular fraction concentration of fetal DNA. The fractional concentration of the fetal DNA can be determined by several methods, including the analysis of fetal-specific epigenetic markers and polymorphic markers between the mother and the father at other loci. Methods for measuring the fractional concentration of both twins in the maternal plasma and the contribution of each fetus are described in US 2013/0059733 A1.

Statistical analysis can be performed on the fractional concentrations of either the A allele or the B allele (or both) to differentiate the three scenarios. The example of each fetus contributing 10% of the total amount of DNA fragments in the sample is still assumed for the following discussion. Embodiments where the fetuses contribute different fetal DNA percentages is addressed in a later section.

Figures 7A, 7B:
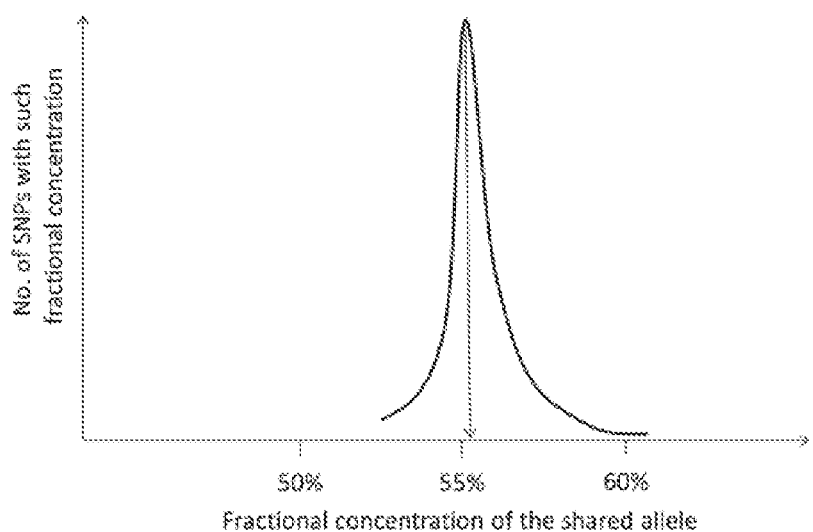
FIG. 7A shows the fractional concentrations of the maternal-specific allele (B allele) and the allele shared by the father and mother (A allele) for the three different scenarios of maternal haplotype inheritance for two fetuses.
FIG. 7B illustrates how individual fractional concentrations at each informative SNP locus can be used to estimate the fractional concentration of the shared allele (A allele) for all loci of a particular type.

FIG. 7A shows the fractional concentrations of the maternal-specific allele (B allele) and the allele shared by the father and mother (A allele) for the three different scenarios of maternal haplotype inheritance for two fetuses. In FIG. 7A, it is assumed that each of the two fetuses contributed 10% of the total maternal plasma DNA, and the predicted fractional concentrations of the shared alleles (A alleles) for type $\alpha$ SNPs and type $\beta$ SNPs. The fractional concentration of the A alleles for the SNP loci can be measured experimentally, and then compared with the predicted value to determine which inheritance pattern best is most probable.

The allelic counts for the A and B alleles of all the SNPs of the same type ($\alpha$ or $\beta$) within the region-of-interest can be aggregated together to calculate the aggregated fractional concentrations for type $\alpha$ and type $\beta$ SNPs. The deviations of the aggregated fractional concentrations from the predicted values can be determined. The pattern that gives the smallest total deviation can be deduced to be the maternal inheritance in the twin fetuses.

In FIG. 7A, the fractional concentrations of the shared alleles (A allele) determined using type $\alpha$ and type $\beta$ SNPs would be the same when one fetus has inherited Hap I and the other has inherited Hap II from the mother. The fractional concentration of the A alleles would be higher for the type $\alpha$ SNPs than for the type $\beta$ SNPs if both fetuses have inherited Hap I from the mother. In contrast, the fractional concentration would be higher for the type $\beta$ SNPs than for the type $\alpha$ SNPs if both fetuses have inherited the maternal Hap II.

The fractional concentrations of the shared alleles (A allele) using type $\alpha$ and type $\beta$ SNPs can be compared to determine if they are statistically different. For example, if the fractional concentrations of the shared alleles based on type $\alpha$ and type $\beta$ SNPs are not statistically different, one fetus has inherited Hap I and one has inherited Hap II from the mother. Alternatively, if the fractional concentration of the shared alleles for the type α SNPs is statistically significantly higher than that for the type β SNPs, both fetuses have inherited Hap I from the mother. If the fractional concentration of the shared alleles for the type α SNPs is statistically significantly lower than that for the type β SNPs, it indicates that both fetuses have inherited Hap II from the mother.

In another embodiment, a ratio of the fractional concentrations (or other amounts) for type α loci and type β loci can be computed. This ratio can be compared to the ratios in column 710.

Different statistical tests can be used to determine if the fractional concentrations of the shared allele for the type α and type β SNPs are significantly different. Examples of these methods include (but not limited to) sequential probability ratio testing (SPRT), Student's t test, Mann-Whitney rank-sum test, Chi square test.

FIG. 7B illustrates how individual fractional concentrations at each informative SNP locus can be used to estimate the fractional concentration of the shared allele (A allele) for all loci of a particular type. The distribution of the fractional concentrations for all the SNP loci can then be constructed and the measured fractional concentration can be determined from the peak of the distribution. This statistical analysis can be performed instead of summing counts of all A alleles and counts of all B alleles.

Accordingly, individual ratios (e.g., fractional concentrations) of amounts at each locus can be computed. These individual ratios can then be used to obtain an overall ratio (e.g., an overall fractional concentration). Thus, an average, median, or other statistical value (e.g., peak of a distribution) of individual ratios can be used to determine an overall ratio that may be compared to a cutoff.

C. Scheme for Determining Maternal Inheritance Using Both Types of Loci

In one embodiment, both types of loci can be used in a quantitative process to determine the inheritance of the maternal haplotypes. For example, the type α loci can be used to determine whether both fetuses have inherited a same haplotype. And, the type β loci can be used to determine whether each fetus inherits a different haplotype.

Figure 8:
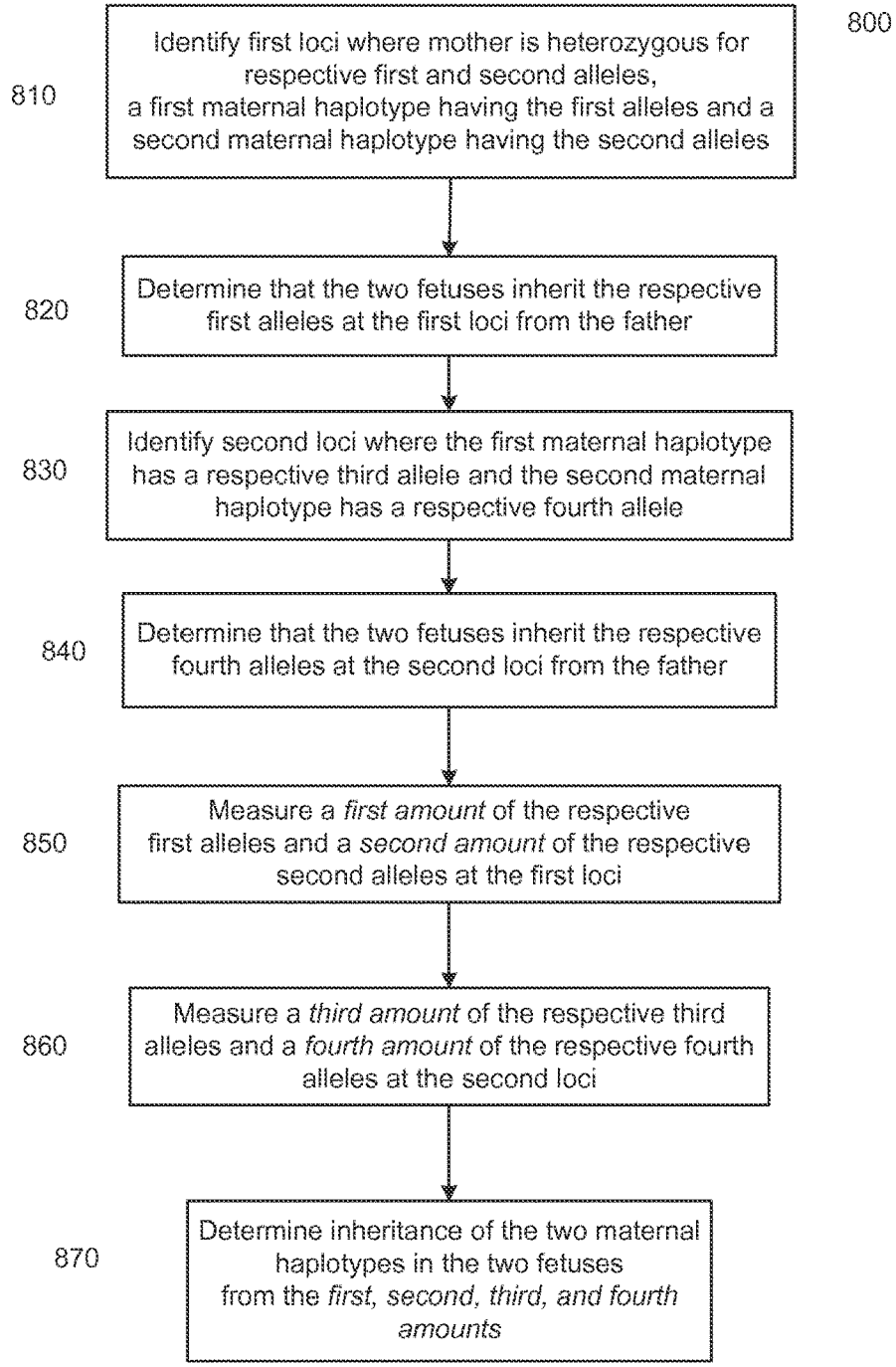
FIG. 8 is a flowchart of a method 800 for determining inheritance of a maternal haplotype using both types of loci according to embodiments of the present invention.

FIG. 8 is a flowchart of a method 800 for determining inheritance of a maternal haplotype using both types of loci according to embodiments of the present invention. Method 800 can analyze maternal inheritance in dizygotic twin fetuses. The analysis is done on a sample obtained from the female parent, where the sample contains the maternal DNA and fetal DNA (e.g., cell-free DNA) from each of the fetuses. Any biological sample (e.g., as defined herein) can be used, provide the sample contains fetal DNA. As with other methods, method 800 uses a computer system.

At block 810, a first group of one or more first loci are identified on a first chromosome. The female is heterozygous for a respective first allele and a respective second allele at each first locus. The first maternal haplotype has the first alleles and a second maternal haplotype has the second alleles. The first loci may be near a genetic feature of interest on a particular chromosome. The first group of loci can correspond to the type α loci described in examples herein.

At block 820, it is determined that the two fetuses inherit the respective first alleles at the first loci from the father. In one embodiment, the father may be determined to be homozygous for the respective first alleles, and thus the first alleles would be inherited regardless of which paternal haplotype is inherited. This genotyping of the father can be performed using a paternal sample. In another embodiment, method 200 can be used to determine an inherited paternal haplotype. Since the paternal haplotype is determined, the paternally-inherited allele at the first loci can be determined, even if the father is heterozygous at the first loci.

Accordingly, if paternal inheritance is determined first, it is not necessary to limit the analysis of maternal inheritance to loci where the father is homozygous and the mother is heterozygous. Loci where both parents are heterozygous can also be used, because the parental inheritance dictates which paternal allele(s) have been passed on to the two fetuses. Based on that information, the loci can be classified as falling into the first group or the second group.

At block 830, a second group of one or more second loci are identified on the first chromosome. The first maternal haplotype has a respective third allele and the second maternal haplotype has a respective fourth allele at each second locus of the second group. The first group of loci can correspond to the type β loci described in examples herein.

At block 840, it is determined that the two fetuses inherit the respective fourth alleles at the second loci from the father. The determination of the inheritance of the fourth alleles from the father can be determined as described above for block 820. For example, the father can be homozygous for the respective fourth allele at each locus of the second loci. In another embodiment, the father can be heterozygous at the second loci, but other loci can be used to determine that the respective fourth allele is inherited from a particular paternal haplotype using method 200, which can use a different set of loci (e.g., ones where the mother is homozygous).

At block 850, a computer system measures a first amount of the respective first alleles and a second amount of the respective second alleles that are present at the first loci in DNA fragments of the biological sample from the female. For example, DNA fragments can be sequenced to obtain sequence reads, and the reads can be aligned to a reference genome to identify reads aligning to the first loci. The number of reads having the first and second alleles can be counted to determine the first and second amounts, respectively. In other embodiments, other techniques are used as mentioned herein or in incorporated documents.

At block 860, the computer system measures a third amount of the respective third alleles and a fourth amount of the respective fourth alleles that are present at the second loci in DNA fragment of the biological sample. The third and fourth mounts can be computed in a similar manner as the first and second amounts.

In some embodiments, the amounts can be normalized, e.g., to determine a fractional concentration of a particular allele. Thus, the first amount can correspond to a count of DNA fragments with the first alleles divided by the total number of DNA fragments at all of the first loci. A normalization of the second amount can be determined in a similar manner. A normalization of the third and fourth amounts can be determined using a total number of DNA fragments at the second loci.

At block 870, the inheritance of maternal haplotypes in the two fetuses is determined using the four amounts. In one embodiment, maternal inheritance is then determined from the four measured amounts as follows:

(i) both fetuses have inherited the first maternal haplotype when the first amount is statistically higher than the second amount and the third amount is statistically equal to the fourth amount;

(ii) both fetuses have inherited the second maternal haplotype when the first amount is statistically equal to the second amount and the fourth amount is statistically higher than the third amount; or (iii) one of the fetuses has inherited the first maternal haplotype and the other has inherited the second maternal haplotype when the first amount is statistically higher than the second amount and when the fourth amount is statistically higher than the third amount.

Whether an amount is statistically higher can be determined by using cutoff values, e.g., requiring a specified number of standard deviations. The cutoffs can depend on the fractional fetal DNA concentration, which may be calculated just for all fetuses and/or for individual fetuses.

In one embodiment, the first amount can be compared directly with the second amount plus a cutoff value. In this manner, the difference between the two amounts can be deemed statistically higher when the first amount is greater than the second amount plus a cutoff value In another embodiment, a parameter is determined from the first amount and the second amount (e.g., a difference or a ratio), and the parameter is compared to a cutoff to see if the first amount is statistically higher than the second amount. The same can be done for other determinations of statistical difference or statistical equality. In one implementation, the cutoff values for different determinations can vary, e.g., the cutoff for (iii) may require less statistical deviation than for (i) and (ii).

As described above, if the percentage of fetal DNA is 20% with each fetus contributing 10%, the determination of statistical equality vs. statistically greater for (i) and (ii) can distinguish between 50% (equality) and 60% (greater). Thus, a cutoff for determining statistical greater might be true if the parameter (e.g., fractional concentration) is greater than 55%, which is halfway between 50% and 60%. A ratio of the first amount to the second amount can also be used, which would provide 1.5 for the instance of 60% being the A allele at type α loci.

For (iii) the determination of statistically greater can distinguish between 50% and 55%. Thus, a cutoff could be between 51-54%, depending on the sensitivity and specificity desired. A ratio of the first amount of the second amount can also be used, which would provide 1.22 for the instance of 55% being the A allele at type α loci.

D. Method for Determining Maternal Inheritance Using One Type of Loci

In some embodiments, only one type of locus is used. For example, FIG. 7A shows three difference ratios of 50%, 55%, and 60% for the type α loci. A ratio can be compared to various cutoffs to discriminate between these different classifications.

Figure 9:
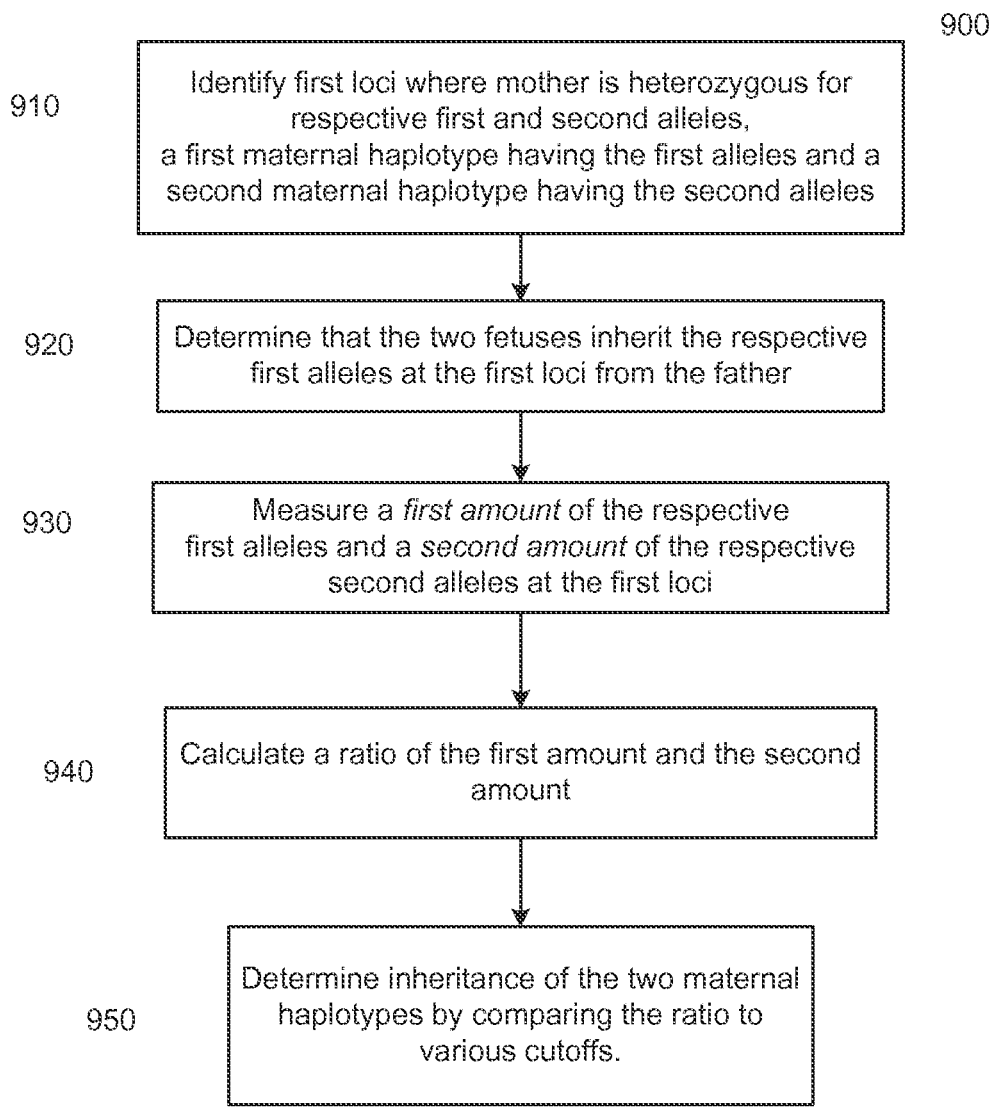
FIG. 9 is a flowchart of a method 900 for determining inheritance of a maternal haplotype using one type of loci according to embodiments of the present invention.

FIG. 9 is a flowchart of a method 900 for determining inheritance of a maternal haplotype using one type of loci according to embodiments of the present invention. Method 900 uses data from a maternal biological sample that includes DNA (e.g., cell-free DNA) from the mother and the fetuses.

At block 910, a first group of one or more first loci are identified on a first chromosome. The mother is heterozygous for a respective first allele and a respective second allele at each first locus. A first maternal haplotype has the first alleles and a second maternal haplotype has the second alleles. Block 910 may be performed in a similar manner as block 810.

At block 920, it is determined that the two fetuses inherit the respective first alleles at the first loci from the father. Block 920 may be performed in a similar manner as block 820. As described above, various steps can be performed in various orders. For example, the data for the parental genomes can be obtained before, during, or after analysis of the maternal sample and may use any suitable DNA technology (e.g., sequencing or PCR).

At block 930, a computer system measures a first amount of the respective first alleles and a second amount of the respective second alleles that are present at the first loci in DNA fragments of the maternal biological sample. Block 920 may be performed in a similar manner as block 850.

At block 940, a ratio of the first amount and the second amount is calculated. The ratio can be of various forms. For example, the first amount divided by the second amount; the second amount divided by the first amount; the first divided by a sum of the first amount and second amount; or the second amount divided by a sum of the first amount and second amount.

At block 950, the inheritance of maternal haplotypes in the two fetuses is determined using the ratio. In one embodiment, maternal inheritance is then determined from the four measured amounts as follows:

(i) identifying both fetuses as having inherited the first maternal haplotype when the ratio is greater than a first cutoff;
(ii) identifying both fetuses as having inherited the second maternal haplotype when the ratio is less than a second cutoff; or
(iii) identifying one of the fetuses as inheriting the first maternal haplotype and the other fetus as inheriting the second maternal haplotype when the ratio is less than a third cutoff and greater than a fourth cutoff, the third cutoff being less than or equal to the first cutoff, and the fourth cutoff being greater than or equal to the second cutoff and less than the third cutoff.

The cutoff values used in this analysis can be determined from the relative amount or percentage of DNA from each fetus in the maternal sample. The cutoffs can discriminate between the various classifications. In the example of FIG. 7A, the first cutoff can discriminate between 60% and 55%, and specifically determine whether the sample can be classified as both fetuses inheriting Hap I. The third cutoff value can be less than the first cutoff when there is an undetermined range, as may occur to obtain greater specificity. The second cutoff can discriminate between 50% and 55%, and specifically determine whether the sample can be classified as both fetuses inheriting Hap II. The fourth cutoff can be greater than the second cutoff when there is an undetermined range, as may occur to obtain greater specificity.

In one embodiment, for determining maternal inheritance directly from the fractional concentration of the alleles shared between the male and female patients, two cutoff values are established. There are three scenarios where both fetuses, one fetus, or neither fetus has inherited the respective haplotype. Each scenario will each form a distribution of the fractional concentration of linked alleles of the nature shown in FIG. 7B, with decreasing medians. For example, if both fetuses contribute 5% of the DNA in the biological sample, the fractional concentration for the three scenarios will have a median of about 60%, 55%, and 50% respectively (FIG. 7A). Cutoff values are set to partition between the scenarios. The first or higher cutoff distinguishing inheritance by two fetuses rather than one would be set at about 57.5%. The second or lower cutoff distinguishing inheritance by one fetus rather than neither would be set at about 52.5%.

The paternal genome sequence can be obtained by sequencing a biological sample from the father. The maternal genome sequence can be obtained by sequencing a biological sample taken before the pregnancy, or from a biological sample that contains essentially no fetal DNA, such as exsanguinated tissue or hair follicles. Alternatively, relevant parts of the genome of the male parent and/or the female parent may be deduced by quantitative assessment of the maternal plasma or sample taken during pregnancy.

The loci for analysis are also selected on the basis of their proximity to a particular chromosomal region or genetic feature of interest. The first loci may be selected as there are close to each other and will segregate with the parental haplotypes as long as there has not been a chromosomal cross-over in between them. The user can enlarge or reduce the region of the chromosome being analyzed. Enlarging the region increases precision of the analysis, because more of the DNA in the maternal sample will be relevant. However, enlarging the region also risks the occurrence of a cross-over event in between, in which case inheritance of an allele cannot accurately predict inheritance of the haplotype.

In one embodiment, the ratio of the alleles at each locus is then calculated as the count of each of the alleles separately divided by the count of all alleles together. Increasing the number of reads of the maternal sample increases accuracy of the assessment. Each locus may be analyzed separately and the results combined for consensus, e.g., as depicted in FIG. 7B. Alternatively, counts of alleles at all of the loci are summed together.

E. Fetuses Contributing Different Amounts of DNA to Maternal Plasma

When a pregnant woman is carrying twin fetuses, the two fetuses can release different amounts of DNA into the maternal circulation. As a result, the fractional fetal DNA concentrations from the two fetuses can be different.

FIG. 10A shows the fractional concentrations of the shared allele (A allele) in the maternal plasma for type α and type β SNPs when both fetuses have inherited Hap I from the mother when the fetuses contribute different fetal DNA percentages. In this example, fetus 1 contributes a % and fetus 2 contributes b %. For type β loci, the percentage stays at 50% since both alleles are equal. But, the percentage for type α loci change, as the A allele is more abundant. The percentage follows the formula of F=50%+(a %+b %)/2.

FIG. 10B shows the fractional concentrations of the shared allele (A allele) in the maternal plasma for type α and type β SNPs when both fetuses have inherited Hap II from the mother when the fetuses contribute different fetal DNA percentages. In this example, fetus 1 contributes a % and fetus 2 contributes b %. For type α loci, the percentage stays at 50% since both alleles are equal. But, the percentage for type β loci change, as the A allele is more abundant. The percentage follows the formula of F=50%+(a %+b %)/2.

FIG. 11A shows the fractional concentrations of the shared allele (A allele) in the maternal plasma for type α and type β SNPs when one fetus inherits Hap I and the other fetus inherits Hap II from the mother when the fetuses contribute different fetal DNA percentages. In this example, fetus 1 contributes a % and fetus 2 contributes b %. For both loci, the percentage of the abundant allele varies with the fetal contribution. For type α loci, the percentage becomes F=50%+a %/2. And, the percentage for type β loci becomes F=50%+b %/2.

FIG. 11B shows a table 1150 of the fractional concentrations of A alleles using type α and β SNPs and the ratio of these two concentrations in the three scenarios, namely both fetuses have inherited the maternal Hap I, both fetuses have inherited the maternal Hap II and the two fetuses have inherited different maternal haplotypes. Column 1160 shows the expected ratio for the shared allele A for type α loci corresponding to the three scenarios. Column 1160 shows the expected ratio for the shared allele A for type β loci corresponding to the three scenarios. Column 1180 shows a ratio of the parameters from the other columns, namely ratio of the values for type α relative to values for type β. As described in the next section, embodiments can use the values in column 1180 to determine cutoffs for a ratio of the concentrations from both types of loci.

F Method Using Ratios of Ratios

In one embodiment, method 900 can use a ratio (e.g., as in column 1180 of the ratios for type α and β). For example, the ratio used in block 940 can be the ratio in column 1180. To use such a ratio, both types of loci are used. Additionally, method 800 can be performed using the ratio in column 1180. Such a method is described below.

Figure 12:
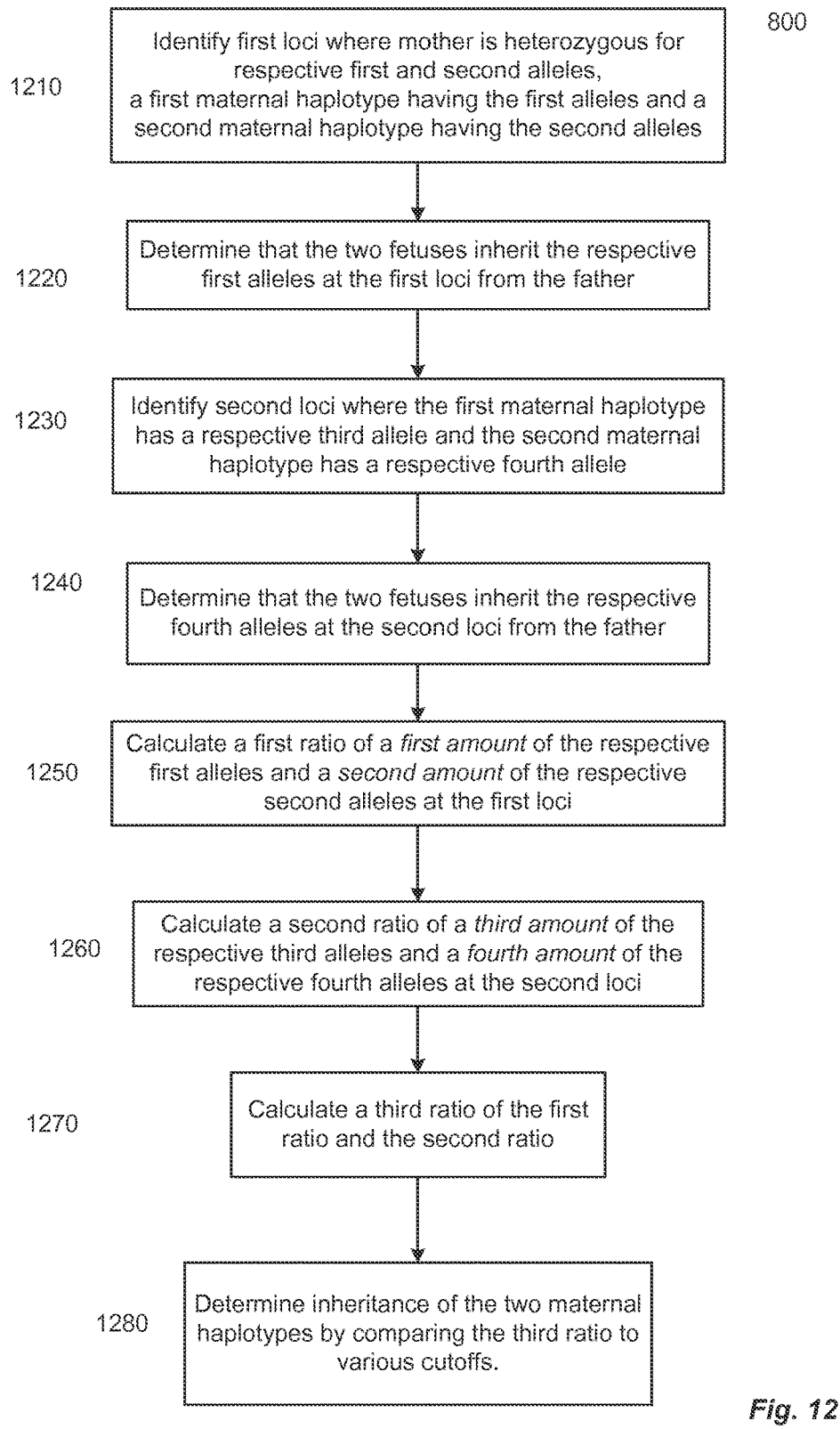
FIG. 12 is a flowchart of a method 1200 for determining inheritance of a maternal haplotype using a ratio of values from both types of loci according to embodiments of the present invention.

FIG. 12 is a flowchart of a method 1200 for determining inheritance of a maternal haplotype using a ratio of values from both types of loci according to embodiments of the present invention. Method 1200 uses data from a maternal biological sample that includes DNA (e.g., cell-free DNA) from the mother and the fetuses.

Blocks 1210-1240 can be performed in a same manner as blocks 810-840 of method 800.

At block 1250, a first ratio is calculated of a first amount of the respective first alleles and a second amount of the respective second alleles that are present at the first loci in DNA fragments of the maternal biological sample. In one embodiment, the first ratio is the first amount divided by the second amount. In another embodiment, the first ratio is of the first amount divided by a sum of the first amount and the second amount to provide a fractional concentration of the first alleles.

At block 1260, a second ratio is calculated of a third amount of the respective third alleles and a fourth amount of the respective fourth alleles that are present at the second loci in DNA fragment of the biological sample. As described herein, the first, second, third, and fourth amounts are obtained from a measurement of the biological sample, e.g., using sequencing or PCR data.

At block 1270, a third ratio is calculated of the first and second ratio. In one embodiment, the third ratio is the third amount divided by the fourth mount, as shown in FIG. 11B. In another embodiment, the third ratio is of the third amount divided by a sum of the third amount and the fourth amount.

At block 1280, the inheritance of maternal haplotypes in the two fetuses is determined using the ratio. In one embodiment, maternal inheritance is then determined from the four measured amounts as follows:
 (i) identifying both fetuses as having inherited the first maternal haplotype when the third ratio is greater than a first cutoff,
 (ii) identifying both fetuses as having inherited the second maternal haplotype when the third ratio is less than a second cutoff, the first cutoff being larger than the second cutoff, or
 (iii) identifying one of the fetuses as inheriting the first maternal haplotype and the other fetus as inheriting the second maternal haplotype when the third ratio is less than a third cutoff and greater than a fourth cutoff, the third cutoff being less than or equal to the first cutoff, and the fourth cutoff being greater than or equal to the second cutoff and less than the third cutoff.

In one embodiment, block 1280 can be performed by first determining whether the first ratio (type α) or the second ratio (Type β) is higher. This can discriminate between whether both fetuses have inherited Hap I or Hap II. After such a determination, only one of those options will survive. Then, it can be determined whether third ratio is closer to the two remaining values. For example, if a>b, it can be determined if the ratio of concentrations by type α and type β loci are closer to one of the two values:

$$(a + a\% + b\%) \text{ or } \frac{\left(50\% + \frac{a\%}{2}\right)}{\left(50\% + \frac{b\%}{2}\right)}.$$

The specific cutoff or threshold values used can be determined using any suitable statistical test. Statistical tests, for example but not limited to sequential probability ratio testing (SPRT), normal mixture mode 1 (McLachlan G and Peel D. Multivariate normal mixtures. Finite mixture models 2004: p 81-116. John Wiley & Sons Press), binomial mixture model and Poisson mixture model (McLachlan G and Peel D. Mixtures with non-normal components, Finite mixture models 2004: p 135-174. John Wiley & Sons Press) can be used in methods described herein. For example, a cutoff can determine if the third ratio is statistically different from the two values above. Alternatively, computer simulation can be used to determine which of the true values is more compatible with the ratio value of the tested case (Qu J Z et al. Clin Chem. 2013; 59:427-35).

G. Clinical Assessment

Maternally inherited autosomal diseases can be assessed by analyzing a chromosomal region linked to the disease locus. If the maternal haplotype linked to the disease allele is inherited by both fetuses, then both fetus would be affected by the condition. If the two fetuses are deduced to have inherited different maternal haplotypes, then only one of the fetuses would be affected. If both fetuses inherit the maternal haplotype linked with the normal allele, then both fetuses would not be affected.

Autosomal recessive disease can be assessed by taking into account the inheritance of the paternal haplotypes. If both fetuses inherit the paternal haplotype linked with the disease allele, then based on the analysis of the inheritance of the maternal haplotypes, we can determine if the fetuses would be affected by the condition or would be carriers. If both fetuses inherit the normal paternal allele, then analysis of the inheritance of the maternal haplotypes can determine if the fetuses are carriers of the condition. If the two fetuses inherit different paternal haplotypes and different maternal haplotypes, then there is 50% chance that one fetus is affected and the other is normal and there is 50% chance that both fetuses are carriers of the condition.

IV. Mother and Father are Heterozygous

By extension, the principles behind the embodiments described above can be applied in other patterns of inheritance. As mentioned above, the same paternally-inherited allele can be inherited by both fetuses. And, the paternally-inherited allele can be determined even in instances where the father is heterozygous. For example, the paternally-inherited haplotype can be determined from loci where the mother is homozygous and the father is heterozygous, and then the paternally-inherited alleles at other loci on the haplotype can be determined. But, some embodiments can be used when the paternally-inherited allele is not known.

In one embodiment, maternal inheritance can be determined using loci where both the maternal and paternal genotypes are heterozygous for both the A allele and the B allele, and the paternally inherited alleles are not the same among all fetuses or are not known. Measuring the presence of these two haplotypes in maternal plasma will resolve into five ranges. For example, if the two fetuses each contribute 10% of the DNA in the maternal plasma, the proportional contribution of the A allele measured will be approximately 40% (if both fetuses are homozygous B); 45% (if one fetus is homozygous B and the other is heterozygous); 50% (if both fetuses are heterozygous or if one is homozygous A and the other is homozygous B); 55% (if one fetus is homozygous A and the other is heterozygous); and 60% (if both are homozygous A). To separate the five possible scenarios, four cut-off amounts are defined. To resolve this complexity, typically more DNA reads are needed for the plasma sample than when the parental locus is homozygous A.

Maternal inheritance can also be determined where there is more than two allelic variants at each locus. Thus, if the maternal genotype is AB and the paternal genotype is CD at a particular locus, the amount of DNA measured in maternal plasma will resolve such that the proportional contribution of A will resolve into 40% (if both fetuses are BC or BD), 45% (if the fetuses are AC or AD combined with BC or BD); and 50% (if both fetuses are AC or AD). If the maternal genotype is AB and the paternal genotype is AC, the amount of DNA measured in maternal plasma will resolve into five ranges, as in the case where the parental genotype is AB in terms of the A allele, but lower in terms of the B allele.

Figure 13:
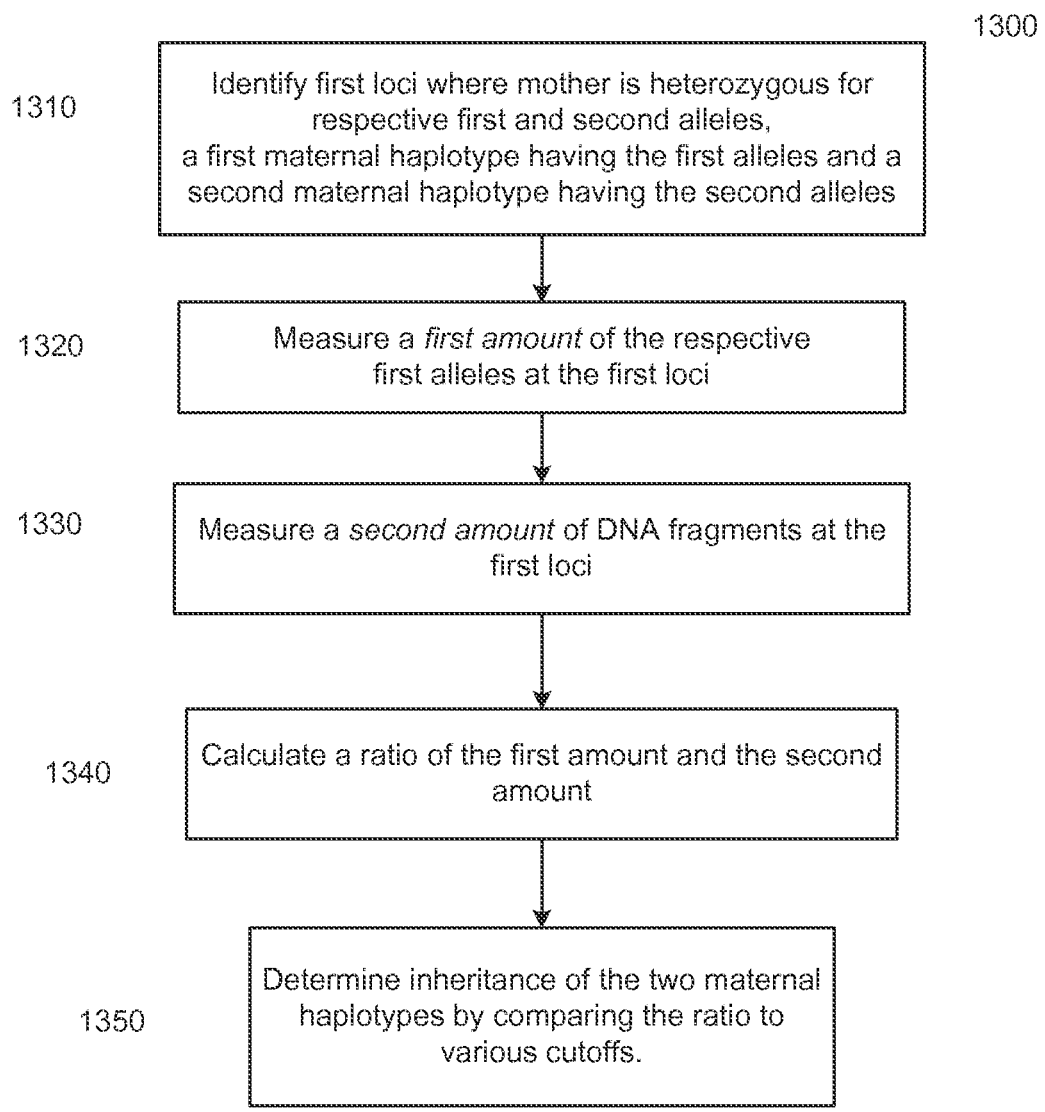
FIG. 13 is a flowchart of a method 1300 of determining inheritance of maternal haplotypes in two fetuses of a female fertilized by a male, where the mother and father are heterozygous, according to embodiments of the present invention.

FIG. 13 is a flowchart of a method 1300 of determining inheritance of maternal haplotypes in two fetuses of a female fertilized by a male, where the mother and father are heterozygous, according to embodiments of the present invention. Method 1300 uses a biological sample from the mother, e.g., which includes cell-free DNA of the female and the two fetuses.

At block 1310 a first group of one or more first loci are identified on a first chromosome. The female is heterozygous for a respective first allele and a respective second allele at each first locus. A first maternal haplotype has the first alleles and a second maternal haplotype has the second alleles. The male is also heterozygous at the first loci. The first group can be either type of loci.

At block 1320, a first amount of the respective first alleles that are present at the first loci in DNA fragments of the biological sample is measured. Block 1320 may be performed in a similar manner as other measuring operations.

At block 1330, a second amount of DNA fragments of the biological sample that are from the first loci is measured. The second amount can correspond to any DNA fragment that is located at one of the first loci. Any signal that indicates a DNA fragment (with any allele) is from one of the first loci can be used to determine the second amount. For example, such a signal can be a sequence read that aligns to one of the first loci or a color of a well in PCR that corresponds to a probe for one of the first loci.

At block 1340, a ratio of the first amount and the second amount is calculated. The ratio can be any ration, e.g., as described herein.

At block 1350, the inheritance of maternal haplotypes in the two fetuses is determined using the ratio. In one embodiment, maternal inheritance is then determined as follows:

(i) identifying both fetuses as having inherited the first maternal haplotype when the ratio is greater than a first cutoff; and (ii) identifying both fetuses as having inherited the second maternal haplotype when the ratio is less than a second cutoff.

Other maternal inheritance can be determined. In some embodiments, a first paternal haplotype has the first alleles and a second maternal haplotype has the second alleles, as in the first example above. When the ratio is statistically equal to 50%, both fetuses can be identified as being heterozygous at the one or more first loci (e.g., At block), or one fetus is homozygous for the first alleles (e.g., AA) and the other fetus is homozygous for the second alleles (e.g., BB). Another example includes identifying that one fetus is homozygous for the second alleles (e.g., BB) and the other fetus is heterozygous (e.g., AB) at the one or more first loci when the ratio is greater than the second cutoff (e.g., to discriminate between 40% and 45% in example above) and less than a third cutoff (e.g., to discriminate between 45% and 50% in example above). Thus, the third cutoff is less than the first cutoff. Another example includes identifying that one fetus is homozygous for the first alleles (e.g., AA) and the other fetus is heterozygous (e.g., At block) at the one or more first loci when the ratio is less than the first cutoff (e.g., to discriminate between 60% and 55% in example above) and greater than a fourth cutoff (e.g., to discriminate between 50% and 55% in example above). Thus, the fourth cutoff is greater than the third cutoff.

In some embodiments, a first paternal haplotype has respective third alleles (e.g., C) and a second paternal haplotype has respective fourth alleles (e.g., D). When the ratio is less than the first cutoff and greater than the second cutoff, one fetus can be identified as heterozygous for the first alleles and either of the third or fourth alleles (e.g., AC or AD). The other fetus can be identified as heterozygous for the second alleles and either of the third or fourth alleles (e.g., BC or BD).

V. Triplets

Maternal inheritance can also be resolved according to the principles of this invention in pregnancies involving more than two fetuses. For example, consider the example when the mother is heterozygous AB and the father is homozygous AA, and there are three fetuses (triplets) each contributing 10% of the DNA in the maternal plasma sample. The proportional contribution of A will resolve into 50% (if all three fetuses are heterozygous); 55% (if two are heterozygous and one is homozygous A); 60% (if one is heterozygous and two are homozygous A); and 65% (if all three are homozygous A). For multiple pregnancies higher than two, typically more DNA reads are needed for the plasma sample to provide ample resolution.

Accordingly, in one embodiment, the three fetuses can be identified as heterozygous at the one or more first loci when the first amount is statistically equal to the second amount (e.g., ~50% value for the ratio). When the ratio is less than a third cutoff (e.g., to discriminate between 60% and 55%) and greater than a fourth cutoff (e.g., to discriminate between 50% and 55%), two fetuses can be identified as heterozygous and one fetus as homozygous for the first alleles at the one or more first loci. When the ratio is greater than the first cutoff (e.g., to discriminate between 60% and 55%) and less than a fifth cutoff (e.g., to discriminate between 65% and 60%), two fetuses can be identified as homozygous for the first alleles and one fetus as heterozygous at the one or more first loci. When the ratio is greater than the fifth cutoff, all three fetuses can be identified as homozygous for the first alleles.

VI. Example

The following section provides a non-limiting working example that illustrates some of the principles of this invention.

A. Obtaining and Measuring Fetal DNA from Dizygotic Twins

Two pregnant women each with twin pregnancies were recruited in the Department of Obstetrics and Gynaecology of the Prince of Wales Hospital, Hong Kong with informed consent. Blood samples were collected at 21 and 25 weeks of gestation. Cord blood was collected separately from each fetus after delivery. This study was approved by the Joint Chinese University of Hong Kong—Hospital Authority New Territories East Cluster Clinical Research Ethics Committee.

Maternal blood samples were centrifuged at 1,600 g for 10 min at 4° C. The plasma portion was recentrifuged at 16,000 g for 10 min at 4° C. to remove any residual blood cells. The blood cell portion was recentrifuged at 2,500 g for 5 min at room temperature to remove any residual plasma. Plasma DNA was extracted with the DSP™ DNA Blood Mini Kit™ (Qiagen). Cord blood DNA was extracted with the QIAamp™ DNA Blood Mini Kit™ (Qiagen). Genomic DNA extracted from cord blood samples was genotyped with the Affymetrix™ Genome-Wide Human SNP Array 6.0 System™ (Affymetrix). The two pairs of twins in each subject were confirmed to be dizygotic by the genotype analysis.

Plasma DNA sequencing libraries were constructed with the Paired-End Sample Preparation Kit™ (Illumina). Approximately 30 ng of DNA was used to prepare each library. These libraries were then subjected to target enrichment using the custom-designed SureSelect Target Enrichment System™ (Agilent Technologies). The capture library covered 5.5 Mb of genomic regions distributed over 14 chromosomes (chr) as follows: chr1 (0.33 Mb), chr2 (0.30 Mb), chr3 (0.62 Mb), chr4 (0.32 Mb), chr5 (0.33 Mb), chr7 (0.31 Mb), chr8 (0.62 Mb), chr9 (0.31 Mb), chr13 (0.30 Mb), chr15 (0.33 Mb), chr17 (0.66 Mb), chr19 (0.35 Mb), chr20 (0.34 Mb), and chr22 (0.30 Mb).

The libraries were sequenced by the standard paired-end protocol (Illumina) on a Hi-Seq 2000 sequencer (Illumina), with a read length of 50 bp for each end. Each library was sequenced with 2 lanes of a sequencing flow cell. The SOAP2 algorithm was used to align all sequenced reads to the non-repeat-masked human reference genome (Hg18).

The fractional concentration of fetal DNA was determined by the fractional concentration of the paternally-inherited fetal allele in the maternal plasma. The paternally-inherited fetal allele was identified using the based on its presence as a minor allele at any SNP locus with two different alleles in the maternal plasma.

Based on the distribution of the fractional concentration of the paternally-inherited fetal alleles in the maternal plasma, the total fractional concentrations of the fetal DNA in maternal plasma was estimated. The fractional fetal DNA concentrations were determined as 22.6% and 30.6% for Cases 1 and 2, respectively. The distributions of the fractional concentrations of fetal DNA at all the informative loci were used to determine the contribution of individual twin fetus to the maternal plasma DNA.

B. Analysis and Conclusions

The informative loci for the purposes of this analysis were those SNP loci that the mother is homozygous but at least one fetus is heterozygous and has inherited a different allele from the father. For Case 1, the fractional fetal DNA concentrations in the maternal plasma contributed by the two fetuses were 10% and 11.6%. For Case 2, the fractional fetal DNA concentrations in the maternal plasma contributed by the two fetuses were 12.4% and 18.2%.

For each pregnant woman, RHDO analysis was carried out to determine if the two fetuses had inherited the same or different maternal haplotype. A region located at the long arm of chromosome 4 was used in this example to illustrate the RHDO analysis. According to the genotype analysis of the cord blood of the fetuses, the two fetuses had inherited different maternal haplotypes for this region for Case 1. For Case 2, the two fetuses had inherited the same maternal haplotype. The paternal genotype was determined using family analysis. In this RHDO analysis, only SNP loci that the mother was heterozygous and the father was homozygous were used. In other embodiments, when the inheritance of paternal haplotype is determined, SNP loci that both the mother and father are heterozygous can also be used for RHDO analysis.

In this analysis, a likelihood ratio threshold was used to determine if the fractional concentration determined using the Type $\alpha$ and Type $\beta$ SNPs ($\alpha/\beta$ ratio) is most compatible with which maternal haplotype inheritance pattern of the twin fetuses. For each case, a simulation analysis was performed for the $\alpha/\beta$ ratio based on the fractional concentration of the two fetuses. 5,000 data points were generated in a binomial distribution to simulate sequence reads of the distributions of fractional concentration of the shared alleles for Type $\alpha$ SNPs and Type $\beta$ SNPs. The distributions of the $\alpha/\beta$ ratio for the scenarios that (a) both fetuses have inherited the same maternal haplotype, or (b) the two fetuses have inherited different maternal haplotypes were determined.

Figure 14A:
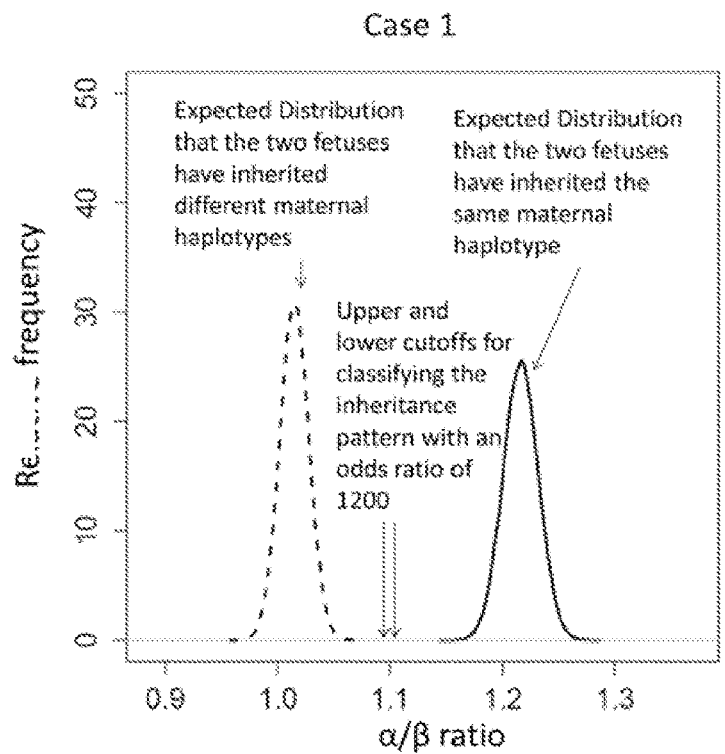
FIGS. 14A and 14B show the distributions of the expected α/β ratio for Case 1 and Case 2, respectively.
Figure 14B:
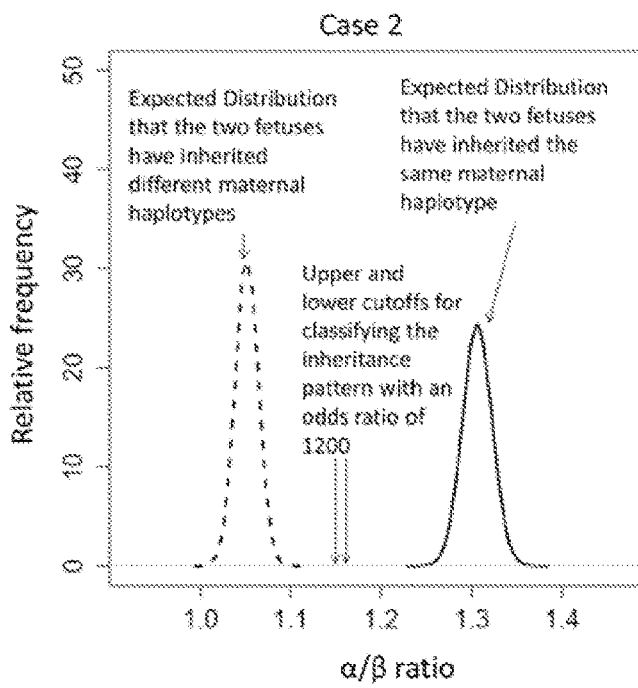

FIGS. 14A and 14B show the distributions of the expected $\alpha/\beta$ ratio for Case 1 and Case 2, respectively. Based on the expected distributions of the $\alpha/\beta$ ratio for the two possible inheritance patterns, a cutoff amount was determined to distinguish whether the two fetuses have inherited the same or different maternal haplotypes. In this particular example, an odds ratio of 1200 was used for calculating the upper and lower cutoff values. An $\alpha/\beta$ ratio greater than the upper cutoff values suggests that the two fetuses have inherited the same maternal haplotype and an $\alpha/\beta$ ratio smaller than the lower cutoff values suggests that the two fetuses have inherited two different maternal haplotypes. For Case 1, the upper and lower cutoff values deduced from the simulation analysis are 1.113 and 1.098, respectively. For Case 2, the upper and lower cutoff values deduced from the simulation analysis are 1.170 and 1.158, respectively.

FIG. 15 is a table 1500 showing the RHDO analysis of a chromosomal segment on the long arm of chromosome 4 for Case 1. As the statistical power of this analysis is dependent on the number of sequenced reads analyzed, 5,000 was used as a threshold requirement for the number of sequenced reads in the classification block. In other words, the number of SNPs in each RHDO classification block would be variable and the total sequenced reads of these SNP loci in the analysis would be more than 5,000. For the first RHDO classification block, the $\alpha/\beta$ ratio was determined as 0.97837 which was smaller than the lower cutoff value, 1.098, deduced from the simulation analysis.

This result is that that the two fetuses had inherited two different maternal haplotypes for this region. SNPs that are downstream of the first classification block were used for further RHDO analysis and the result was suggestive of the inheritance of different maternal haplotypes by the two fetuses. A total of 9 RHDO classification blocks within this region showed the same conclusion. These results were confirmed to be correct by the genotype results of the two fetuses.

FIG. 16 is a table 1600 showing the RHDO analysis of a chromosomal segment on the long arm of chromosome 4 for Case 2. For the RHDO classification block 1, the $\alpha/\beta$ ratio was determined as 1.299, which is larger than the upper cutoff value, 1.170, deduced from the simulation analysis.

This result indicates that that the two fetuses had inherited the same maternal haplotypes for this region. In addition, the fractional concentration determined using the Type $\alpha$ SNPs was higher than the fractional concentration determined using the Type $\beta$ SNPs. This indicates that the two fetuses had inherited the maternal Hap I (FIG. 10A).

SNPs that are downstream of the regions in the first classification block were used for further RHDO analysis and a total of nine RHDO classification blocks within this region show the same conclusion. These results were confirmed to be correct by the genotype results of the two fetuses.

VII. Computer System

Figure 17:
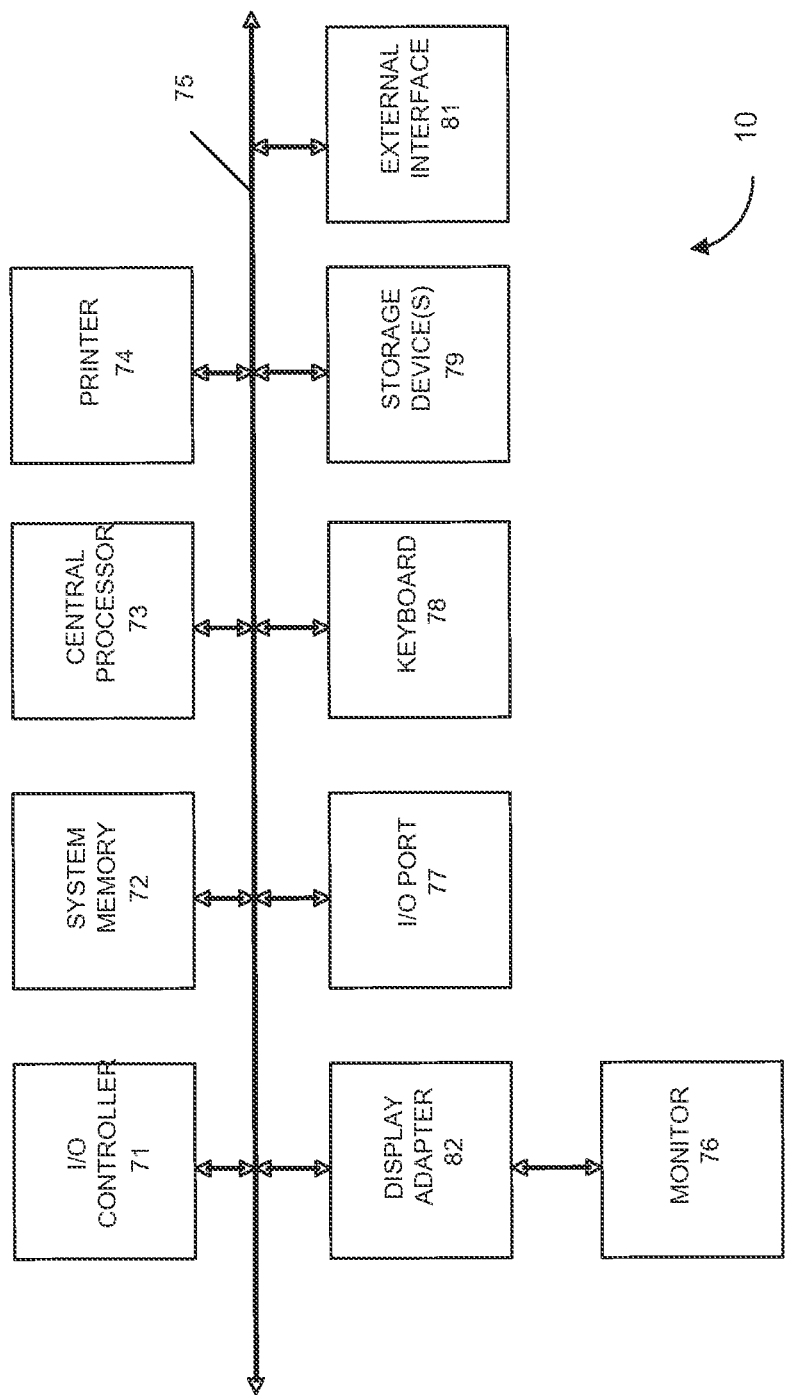
FIG. 17 shows a block diagram of an example computer system 10 usable with system and methods according to embodiments of the present invention.

Any of the computer systems mentioned herein may utilize any suitable number of subsystems. Examples of such subsystems are shown in FIG. 17 in computer apparatus 10. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 17 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 977 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive or optical disk), as well as the exchange of information between subsystems. The system memory 72 and/or the storage device(s) 79 may embody a computer readable medium. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C# or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method of determining inheritance of maternal haplotypes in two fetuses of a female fertilized by a male, the method comprising:
    obtaining a blood sample from the female;
    extracting plasma or serum from the blood sample to obtain a biological sample, the biological sample including cell-free DNA of the female and the two fetuses;
    sequencing, with a sequencing device, DNA fragments from the plasma or serum to obtain sequence reads;
    aligning, by a computer system in communication with the sequencing device, sequence reads to a reference genome to identify reads aligning to a first group of first loci on a first chromosome, wherein the female is heterozygous for a respective first allele and a respective second allele at each first locus, a first maternal haplotype having the first alleles and a second maternal haplotype having the second alleles;
    determining that the two fetuses inherit the respective first alleles at the first loci from the male;
    aligning, by the computer system, sequence reads to the reference genome to identify reads aligning to a second group of second loci on the first chromosome, wherein the first maternal haplotype has a respective third allele and the second maternal haplotype has a respective fourth allele at each second locus of the second group, and
    determining that the two fetuses inherit the respective fourth alleles at the second loci from the male;
    measuring, by the computer system, a first amount of the respective first alleles and a second amount of the respective second alleles that are present at the first loci in DNA fragments of the biological sample from the female, wherein:
        measuring the first amount of respective first alleles includes counting the number of sequence reads aligning to the first loci having the respective first allele, and
        measuring the second amount of respective second alleles includes counting the number of sequence reads aligning to the first loci having the respective second allele;
    measuring, by the computer system, a third amount of the respective third alleles and a fourth amount of the respective fourth alleles that are present at the second loci in DNA fragment of the biological sample, wherein:
        measuring the third amount of respective third alleles includes counting the number of sequence reads aligning to the second loci having the respective third allele, and
        measuring the fourth amount of respective fourth alleles includes counting the number of sequence reads aligning to the second loci having the respective fourth allele; and
    determining inheritance of maternal haplotypes in the two fetuses by:
    (i) identifying both fetuses as having inherited the first maternal haplotype when the first amount is statistically higher than the second amount and the third amount is statistically equal to the fourth amount,
    (ii) identifying both fetuses as having inherited the second maternal haplotype when the first amount is statistically equal to the second amount and the fourth amount is statistically higher than the third amount, or (iii) identifying one of the fetuses as inheriting the first maternal haplotype and the other fetus as inheriting the second maternal haplotype when the first amount is statistically higher than the second amount and when the fourth amount is statistically higher than the third amount.

2. The method of claim 1, further comprising:
determining that the first amount is statistically higher than the second amount and that the third amount is statistically equal to the fourth amount by:
computing a first ratio of the first amount and the second amount;
computing a second ratio of the third amount and the fourth amount;
computing a third ratio of the first ratio and the second ratio; and
comparing the third ratio to a cutoff value.

3. The method of claim 1, further comprising:
determining that the first amount is statistically higher than the second amount and that the fourth amount is statistically higher than the third amount by:
computing a first ratio of the first amount and the second amount;
computing a second ratio of the fourth amount and the third amount;
computing a third ratio of the first ratio and the second ratio; and
comparing the third ratio to a cutoff value.

4. The method of claim 1, wherein the comparison of the third ratio to the cutoff value determines whether the third ratio is statistically equal to one.

5. The method of claim 1, wherein identifying the first group of first loci on a first chromosome includes detecting the respective first and second alleles in the biological sample.

6. The method of claim 1, wherein the male is homozygous for the respective first allele at each first locus of the first group, and the male is homozygous for the respective fourth alleles at each second locus of the second group.

7. The method of claim 1, wherein measuring the first amount of the respective first alleles and the second amount of the respective second alleles includes:
at each first locus:
determining a ratio of a first number of DNA fragments having the respective first allele and a second number of DNA fragments having the respective second allele; and
determining an average ratio of the ratios.

8. The method of claim 7, further comprising:
determining the first amount is statistically higher than the second amount by comparing the average ratio to a cutoff value.

9. The method of claim 1, further comprising:
determining the first amount is statistically higher than the second amount by:
calculating a first parameter from the first amount and the second amount; and
comparing the first parameter to a cutoff.

10. The method of claim 1, wherein one or more of the first alleles, one or more of the second alleles, one or more of the third alleles and/or one or more of the fourth alleles are linked to a phenotype of interest.

11. The method of claim 1, wherein one or more of the second alleles and/or one or more of the fourth alleles is linked to an autosomal dominant disease or disease susceptibility.

12. The method of claim 1, wherein one or more of the first alleles and/or one or more of the second alleles is linked to an autosomal recessive disease or disease susceptibility.

13. The method of claim 1, wherein one or more of the third alleles and/or one or more of the fourth alleles is linked to an autosomal recessive disease or disease susceptibility.

14. The method of claim 1, wherein the biological sample is plasma.

15. A computer product comprising a non-transitory computer readable medium storing a plurality of instructions for controlling a computer system to perform an operation, the instructions comprising the method of claim 1.

16. The method of claim 1, wherein:
determining inheritance of maternal haplotypes in the two fetuses is by a computer system,
further comprising:
displaying, by the computer system, a first result identifying both of the fetuses as having inherited the first maternal haplotype when the first amount is statistically higher than the second amount and the third amount is statistically equal to the fourth amount,
displaying, by the computer system, a second result identifying both fetuses as having inherited the second maternal haplotype when the first amount is statistically equal to the second amount and the fourth amount is statistically higher than the third amount, or
displaying, by the computer system, a third result identifying one of the fetuses as inheriting the first maternal haplotype and the other fetus as inheriting the second maternal haplotype when the first amount is statistically higher than the second amount and when the fourth amount is statistically higher than the third amount.

17. The method of claim 1, wherein the first amount of the respective first allele is at least 2,840.

18. The method of claim 1, wherein:
identifying a first group of one or more first loci on the first chromosome comprises detecting the respective first allele and the respective second allele at loci in DNA fragments of the biological sample,
the one or more first loci comprise a plurality of first loci,
determining that the two fetuses inherit the respective first alleles at the first loci from the male comprises genotyping the male to identify loci where the male is homozygous,
identifying the second group of second loci on the first chromosome comprises detecting the respective third allele and the respective fourth allele at loci in DNA fragments of the biological sample,
the one or more loci comprise a plurality of loci,
determining that the two fetuses inherit the respective fourth alleles at the second loci from the male comprises genotyping the male to identify loci where the male is homozygous.

19. The method of claim 1, wherein determining inheritance of maternal haplotypes in the two fetuses is performed using a computer system executing a maternal inheritance module that:
identifies both fetuses as having inherited the first maternal haplotype when the first amount is statistically higher than the second amount and the third amount is statistically equal to the fourth amount, identifies both fetuses as having inherited the second maternal haplotype when the first amount is statistically equal to the second amount and the fourth amount is statistically higher than the third amount, and identifies one of the fetuses as inheriting the first maternal haplotype and the other fetus as inheriting the second maternal haplotype when the first amount is statistically higher than the second amount and when the fourth amount is statistically higher than the third amount.

20. The method of claim 1, wherein the inheritance of maternal haplotypes is determined when the second amount is less than or equal to 4,166 and the third amount is less than or equal to 3,546.

21. The method of claim 1, wherein the method of determining inheritance of maternal haplotypes in two fetuses of a female fertilized by a male does not use ultrasound scanning or amniocentesis.

22. The method of claim 1, wherein the sequencing of the DNA fragments from the plasma or serum comprises paired-end sequencing.

23. A method of determining inheritance of maternal haplotypes in two fetuses of a female fertilized by a male, the method comprising:
  sequencing, with a sequencing device, DNA fragments from plasma or serum from a blood sample, the plasma or serum including cell-free DNA of the female and the two fetuses;
  aligning, by a computer system in communication with the sequencing device, sequence reads to a reference genome to identify reads aligning to a first group of one or more first loci on a first chromosome, wherein the female is heterozygous for a respective first allele and a respective second allele at each first locus, a first maternal haplotype having the first alleles and a second maternal haplotype having the second alleles;
  determining that the two fetuses inherit the respective first alleles at the first loci from the male;
  measuring a first amount of the respective first alleles and a second amount of the respective second alleles that are present at the first loci in DNA fragments of a biological sample from the female, the biological sample including cell-free DNA of the female and the two fetuses;
  calculating a ratio of the first amount and the second amount;
  determining inheritance of maternal haplotypes in the two fetuses by:
  (i) identifying both fetuses as having inherited the first maternal haplotype when the ratio is greater than a first cutoff,
  (ii) identifying both fetuses as having inherited the second maternal haplotype when the ratio is less than a second cutoff, or
  (iii) identifying one of the fetuses as inheriting the first maternal haplotype and the other fetus as inheriting the second maternal haplotype when the ratio is less than a third cutoff and greater than a fourth cutoff, the third cutoff being less than or equal to the first cutoff, and the fourth cutoff being greater than or equal to the second cutoff and less than the third cutoff.

24. The method of claim 23, wherein calculating the ratio of the first amount and the second amount includes:
  for each first locus, calculating respective ratios of an amount of the respective first allele and an amount of the respective second allele; and
  computing the ratio based on the respective ratios.

25. The method of claim 24, wherein ratio based on the respective ratios includes computing an average or median of the respective ratios.

26. The method of claim 23, wherein the female is pregnant with three fetuses, and wherein determining inheritance of maternal haplotypes in the two fetuses further includes:
  identifying the three fetuses as being heterozygous at the one or more first loci when the first amount is statistically equal to the second amount,
  when the ratio is less than the third cutoff and greater than the fourth cutoff, identifying that two fetuses are heterozygous and one fetus is homozygous for the first alleles at the one or more first loci, or
  when the ratio is greater than the first cutoff and less than a fifth cutoff, identifying that two fetuses are homozygous for the first alleles and one fetus is heterozygous at the one or more first loci, or
  when the ratio is greater than the fifth cutoff, identifying that all three fetuses are homozygous for the first alleles.

27. The method of claim 23, wherein one or more of the first alleles in the first group are linked to a condition or susceptibility, the method further comprising:
  determining whether both, none, or one of the fetuses have inherited the condition or susceptibility based on the inheritance of the haplotypes.

28. The method of claim 23, wherein the female has a haplotype linked to an autosomal recessive condition or susceptibility, and one or both of the fetuses are determined to be carriers of the condition or susceptibility.

29. The method of claim 23, further comprising:
  obtaining a blood sample from the female;
  extracting plasma or serum from the blood sample to obtain the biological sample,
  sequencing, with a sequencing device, the DNA fragments from the plasma or serum to obtain sequence reads,
  aligning, by a computer system in communication with the sequencing device, sequence reads to a reference genome to identify reads aligning to the first loci,
  measuring, by the computer system, the first amount of respective first alleles by counting the number of sequence reads aligning to the first loci having the respective first allele, and
  measuring, by the computer system, the second amount of respective second alleles by counting the number of sequence reads aligning to the first loci having the respective second allele.

30. A method of determining inheritance of maternal haplotypes in two fetuses of a female fertilized by a male, the method comprising:
  sequencing, with a sequencing device, DNA fragments from plasma or serum from a blood sample, the plasma or serum including cell-free DNA of the female and the two fetuses;
  aligning, by a computer system in communication with the sequencing device, sequence reads to a reference genome to identify reads aligning to a first group of one or more first loci on a first chromosome, wherein the female is heterozygous for a respective first allele and a respective second allele at each first locus, a first maternal haplotype having the first alleles and a second maternal haplotype having the second alleles;
  determining that the two fetuses inherit the respective first alleles at the first loci from the male;

aligning, by a computer system in communication with the sequencing device, sequence reads to a reference genome to identify reads aligning to a second group of one or more second loci on the first chromosome, wherein the first maternal haplotype has a respective third allele and the second maternal haplotype has a respective fourth allele at each second locus of the second group, and determining that the two fetuses inherit the respective fourth alleles at the second loci from the male;

calculating a first ratio of a first amount of the respective first alleles and a second amount of the respective second alleles that are present at the first loci in DNA fragments of a biological sample from the female, the biological sample including cell-free DNA of the female and the two fetuses;

calculating a second ratio of a third amount of the respective third alleles and a fourth amount of the respective fourth alleles that are present at the second loci in DNA fragment of the biological sample, wherein the first, second, third, and fourth amounts are obtained from a measurement of the biological sample;

calculating a third ratio of the first and second ratio;

determining inheritance of maternal haplotypes in the two fetuses by:
(i) identifying both fetuses as having inherited the first maternal haplotype when the third ratio is greater than a first cutoff,
(ii) identifying both fetuses as having inherited the second maternal haplotype when the third ratio is less than a second cutoff, the first cutoff being larger than the second cutoff, or
(iii) identifying one of the fetuses as inheriting the first maternal haplotype and the other fetus as inheriting the second maternal haplotype when the third ratio is less than a third cutoff and greater than a fourth cutoff, the third cutoff being less than or equal to the first cutoff, and the fourth cutoff being greater than or equal to the second cutoff and less than the third cutoff.

31. The method of claim 30, wherein the third cutoff is equal to the first cutoff, and the fourth cutoff is equal to the second cutoff.

32. The method of claim 30, further comprising:
determining that the third ratio is greater than a first cutoff by:
comparing the third ratio to one; and
when the third ratio is greater than one, comparing the third ratio to the first cutoff.

33. The method of claim 30, further comprising:
determining that the third ratio is less than a third cutoff and greater than a fourth cutoff by:
determining that the third ratio is statistically equal to one.

34. The method of claim 30, further comprising:
determining a first fractional fetal DNA percentage a % contributed by a first fetus and a second fractional fetal DNA percentage b % contributed by a second fetus, wherein the first, second, third, and fourth cutoffs are determined based on a % and b %.

35. The method of claim 34, wherein the first cutoff discriminates between (1+a %+b %)/1 and (50%+a %/2)/(50%+b %/2).

36. The method of claim 34, wherein the second cutoff discriminates between 1/(1+a %+b %) and (50%+a %/2)/(50%+b %/2).

37. The method of claim 30, wherein step (i) includes determining whether the first ratio is statistically higher than the second ratio, wherein step (ii) includes determining whether second ratio is statistically higher than the first ratio, and wherein step (iii) includes determining that the first ratio and the third ratio are statistically equal.

38. The method of claim 30, further comprising:
obtaining a blood sample from the female;
extracting plasma or serum from the blood sample to obtain the biological sample,
measuring, by the computer system, the first amount of respective first alleles by counting the number of sequence reads aligning to the first loci having the respective first allele,
measuring, by the computer system, the second amount of respective second alleles by counting the number of sequence reads aligning to the first loci having the respective second allele,
measuring, by the computer system, the third amount of respective third alleles by counting the number of sequence reads aligning to the second loci having the respective third allele, and
measuring, by the computer system, the fourth amount of respective fourth alleles by counting the number of sequence reads aligning to the second loci having the respective fourth allele.

39. A method of determining inheritance of maternal haplotypes in two fetuses of a female fertilized by a male, the method comprising:
sequencing, with a sequencing device, DNA fragments from plasma or serum from a blood sample, the plasma or serum including cell-free DNA of the female and the two fetuses;
aligning, by a computer system in communication with the sequencing device, sequence reads to a reference genome to identify reads aligning to a first group of one or more first loci on a first chromosome, wherein the female is heterozygous for a respective first allele and a respective second allele at each first locus, a first maternal haplotype having the first alleles and a second maternal haplotype having the second alleles, and wherein the male is heterozygous at the first loci;
measuring a first amount of the respective first alleles that are present at the first loci in DNA fragments of a biological sample from the female, the biological sample including cell-free DNA of the female and the two fetuses;
measuring a second amount of DNA fragments of the biological sample that are from the first loci;
calculating a ratio of the first amount and the second amount;
determining inheritance of maternal haplotypes in the two fetuses by:
(i) identifying both fetuses as having inherited the first maternal haplotype when the ratio is greater than a first cutoff; and
(ii) identifying both fetuses as having inherited the second maternal haplotype when the ratio is less than a second cutoff.

40. The method of claim 39, wherein a first paternal haplotype has the first alleles and a second maternal haplotype has the second alleles.

41. The method of claim 40, wherein determining inheritance of maternal haplotypes in the two fetuses includes:
when the ratio is statistically equal to 50%, identifying two possibilities of:
both fetuses are heterozygous at the one or more first loci, or one fetus is homozygous for the first alleles and the other fetus is homozygous for the second alleles.

42. The method of claim 40, wherein determining inheritance of maternal haplotypes in the two fetuses includes:
identifying that one fetus is homozygous for the second alleles and the other fetus is heterozygous at the one or more first loci when the ratio is greater than the second cutoff and less than a third cutoff, the third cutoff being less than the first cutoff.

43. The method of claim 42, wherein determining inheritance of maternal haplotypes in the two fetuses includes:
identifying that one fetus is homozygous for the first alleles and the other fetus is heterozygous at the one or more first loci when the ratio is less than the first cutoff and greater than a fourth cutoff, the fourth cutoff being greater than the third cutoff.

44. The method of claim 39, wherein a first paternal haplotype has respective third alleles and a second paternal haplotype has respective fourth alleles.

45. The method of claim 44, wherein determining inheritance of maternal haplotypes in the two fetuses includes:
when the ratio is less than the first cutoff and greater than the second cutoff, identifying possibilities of:
one fetus is heterozygous for the first alleles and either of the third or fourth alleles, and
the other fetus is heterozygous for the second alleles and either of the third or fourth alleles.

46. The method of claim 39, further comprising:
obtaining a blood sample from the female;
extracting plasma or serum from the blood sample to obtain the biological sample,
measuring, by the computer system, the first amount of respective first alleles by counting the number of sequence reads aligning to the first loci having the respective first allele, and
measuring, by the computer system, the second amount of respective second alleles by counting the number of sequence reads aligning to the first loci having the respective second allele.

47. A method of determining inheritance of paternal haplotypes in two fetuses of a female fertilized by a male, the method comprising:
sequencing, with a sequencing device, DNA fragments from plasma or serum from a blood sample, the plasma or serum including cell-free DNA of the female and the two fetuses;
aligning, by a computer system in communication with the sequencing device, sequence reads to a reference genome to identify reads aligning to a first group of one or more first loci on a first chromosome, wherein the male is heterozygous for a respective first allele and a respective second allele at each first locus, a first paternal haplotype having the first alleles and a second paternal haplotype having the second alleles, and wherein the female is homozygous for the second alleles;
measuring a first amount of the respective first alleles that are present at the first loci in DNA fragments of a biological sample from the female, the biological sample including cell-free DNA of the female and the two fetuses;
normalizing the first amount to obtain a normalized first amount;
comparing the normalized first amount to one or more cutoffs;
determining whether one fetus, both fetuses, or none of the fetuses inherited the first paternal haplotype based on the comparison.

48. The method of claim 47, further comprising:
determining a fetal DNA percentage in the biological sample from one or both of the two fetuses; and
determining the one or more cutoffs based on the fetal DNA percentage.

49. The method of claim 47, wherein the normalized first amount is compared to a first cutoff and a second cutoff, wherein none of the fetuses are determined to have inherited the first paternal haplotype when the normalized first amount is less than the second cutoff value, wherein one of the fetuses are determined to have inherited the first paternal haplotype when the normalized first amount is greater than the second cutoff and less than the first cutoff, and wherein both of the fetuses are determined to have inherited the first paternal haplotype when the normalized first amount is greater than the first cutoff.

50. The method of claim 47, wherein normalizing the first amount to obtain a normalized first amount includes:
measuring a second amount of the respective second alleles that are present at the first loci in DNA fragments of the biological sample; and
calculating a ratio of the first amount to the second amount to obtain the normalized first amount.

51. The method of claim 50, wherein the ratio is of the first amount divided by a sum of the first amount and the second amount.

52. The method of claim 47, wherein determining whether one fetus, both fetuses, or none of the fetuses inherited the first paternal haplotype based on the comparison includes:
identifying only one of the fetuses as having inherited the haplotype if the normalized first amount is statistically above zero but below a first cutoff; or
identifying both fetuses as having inherited the haplotype if the normalized first amount is above a second cutoff value.

53. The method of claim 47, further comprising:
identifying a second group of one or more second loci on the first chromosome, wherein the male is heterozygous for a respective third allele and a respective fourth allele at each second locus, the first paternal haplotype having the third alleles and the second paternal haplotype having the fourth alleles, and wherein the female is homozygous for the third alleles;
measuring a second amount of the respective fourth alleles that are present at the second loci in DNA fragments of the biological sample;
normalizing the second amount to obtain a normalized second amount;
comparing the normalized second amount to one or more cutoffs;
determining whether one fetus, both fetuses, or none of the fetuses inherited the second paternal haplotype based on the comparison.

54. The method of claim 53, further comprising:
using the determination of inheritance for the first and second paternal haplotypes to make a determination of whether one fetus, both fetuses, or none of the fetuses inherited the first and second paternal haplotypes.

55. The method of claim 47, wherein one or more of the first alleles and/or one or more of the second alleles is linked to a phenotype of interest.

56. The method of claim 47, wherein the phenotype of interest is a disease or disease susceptibility.

57. The method of claim 47, wherein the first paternal haplotype is linked to an autosomal recessive condition or susceptibility, and one or both of the fetuses are determined to be carriers of the condition or susceptibility.

58. The method of claim 47, further comprising:
- obtaining a blood sample from the female;
- extracting plasma or serum from the blood sample to obtain the biological sample,
- measuring, by the computer system, the first amount of respective first alleles by counting the number of sequence reads aligning to the first loci having the respective first allele, and
- measuring, by the computer system, the second amount of respective second alleles by counting the number of sequence reads aligning to the first loci having the respective second allele.

* * * * *